US012533163B2

(12) United States Patent
Rathbun et al.

(10) Patent No.: US 12,533,163 B2
(45) Date of Patent: Jan. 27, 2026

(54) PEDICLE SCREW DISTRACTOR AND REDUCTION INSTRUMENT

(71) Applicant: Intelivation Technologies LLC, Saint Simons Island, GA (US)

(72) Inventors: David Rathbun, Saint Simons Island, GA (US); Amir Fayyazi, Saint Simons Island, GA (US)

(73) Assignee: Intelivation Technologies LLC, Saint Simons Island, GA (US)

( * ) Notice: Subject to any disclaimer, the term of this patent is extended or adjusted under 35 U.S.C. 154(b) by 180 days.

(21) Appl. No.: 18/379,054

(22) Filed: Oct. 11, 2023

(65) Prior Publication Data

US 2024/0148416 A1 May 9, 2024

Related U.S. Application Data

(60) Provisional application No. 63/415,085, filed on Oct. 11, 2022.

(51) Int. Cl.

| | |
|---|---|
| ***A61B 17/70*** | (2006.01) |
| *A61B 17/02* | (2006.01) |
| *A61B 17/56* | (2006.01) |

(52) U.S. Cl.

CPC .. *A61B 17/7076* (2013.01); *A61B 2017/0256* (2013.01); *A61B 2017/564* (2013.01)

(58) Field of Classification Search

CPC ............ A61B 17/7076; A61B 17/7077; A61B 17/708; A61B 2017/0256; A61B 2017/564; A61B 2017/681

See application file for complete search history.

(56) References Cited

U.S. PATENT DOCUMENTS

| | | | | |
|---|---|---|---|---|
| 7,008,432 | B2 * | 3/2006 | Schlapfer ........... | A61B 17/8866 606/90 |
| 9,066,763 | B2 * | 6/2015 | Khoo ................. | A61B 17/7086 |
| 9,387,017 | B2 * | 7/2016 | Stad .................. | A61B 17/7074 |
| 9,833,267 | B2 * | 12/2017 | King .................. | A61B 17/7037 |

* cited by examiner

*Primary Examiner* — Anu Ramana

(74) *Attorney, Agent, or Firm* — Meunier Carlin & Curfman LLC

(57) ABSTRACT

A pedicle screw distractor and reduction instrument that includes a main body including a distraction tab and a reduction foot; a secondary link pivotably mounted to the main body; a drive link coupled between the secondary link and the distraction aperture; a distraction actuator coupled to the drive link and structured to move the main body relative the secondary link; a proximal anchor pivotably coupled to the secondary link and including a proximal anchor foot configured to engage a proximal pedicle screw; a distal anchor pivotably coupled to the main body and including a distal anchor foot configured to engage a distal pedicle screw; and a reduction actuator engaged between the reduction foot and the distal anchor to move the distal anchor foot relative to the main body.

20 Claims, 30 Drawing Sheets

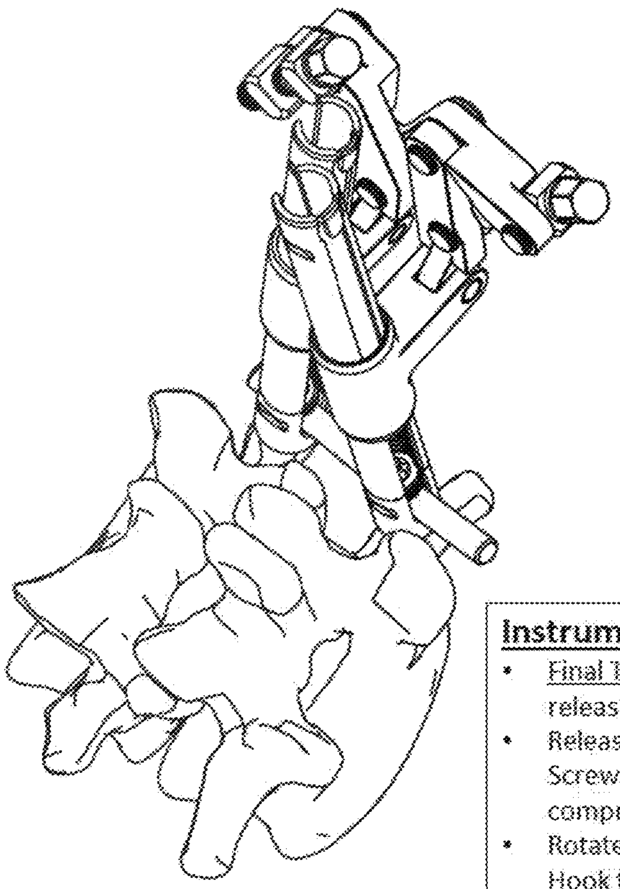

FIG. 43

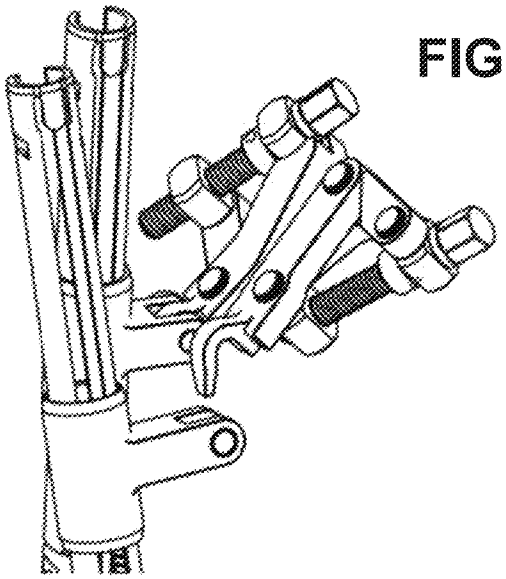

FIG. 44

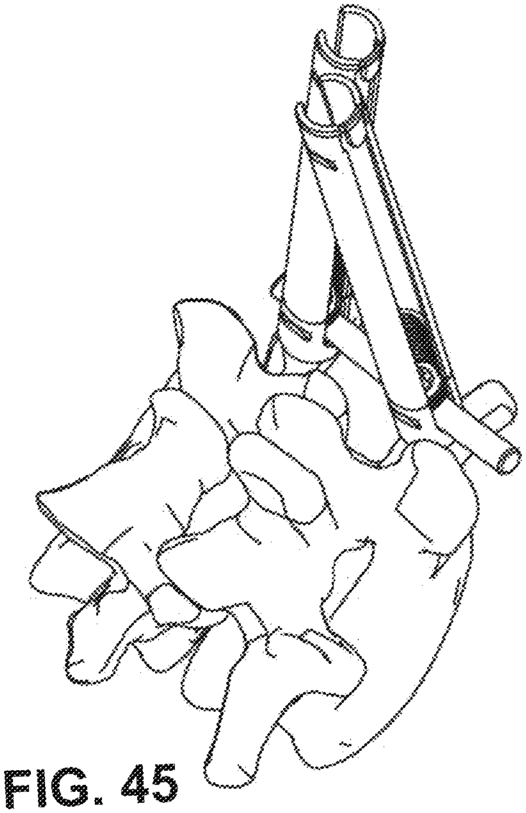

FIG. 45

Instrument Disengagement

- Final Tighten - Torque Locking Caps prior to releasing tension or compression on the device
- Release tension or compression by turning Black Screw in opposite direction that was used to compress or distract
- Rotate instrument approximately 45° to release Hook from MIS Tower Adapter
- Slide both components off the proximal ends of towers

PEDICLE SCREW DISTRACTOR AND REDUCTION INSTRUMENT

CROSS-REFERENCE TO RELATED APPLICATIONS

This application claims the benefit of U.S. Provisional Patent Application No. 63/415,085 filed on Oct. 11, 2022, the entire contents of which are incorporated herein by reference.

BACKGROUND

This disclosure relates to pedicle screw distractor and reduction instruments.

SUMMARY

One implementation relates to a pedicle screw distractor and reduction instrument that includes a main body defining a first pivot axis and a second pivot axis, the main body including a central bar extending between the first pivot axis and the second pivot axis, a distraction tab extending obliquely from the central bar and defining a distraction aperture, and a reduction foot extending obliquely from the central bar and defining a race; a secondary link pivotably mounted to the main body at the first pivot axis and defining a third pivot axis spaced apart from and parallel to the first pivot axis and the second pivot axis; a drive link coupled to the secondary link at the third pivot axis and received within the distraction aperture; a distraction actuator coupled to the drive link and structured to move the main body relative the secondary link about the first pivot axis; a proximal bar pivotably coupled to the secondary link about the third pivot axis and defining a proximal bar aperture; a proximal anchor received through the proximal bar aperture and including a proximal anchor foot configured to engage a proximal pedicle screw; a distal anchor pivotably coupled to the main body about the second pivot axis and including a distal anchor tab, and a distal anchor foot configured to engage a distal pedicle screw; and a reduction actuator engaged with the distal anchor tab and the race of the reduction foot to move the distal anchor foot relative to the main body about the second pivot axis.

Another implementation relates to a pedicle screw distractor and reduction instrument that includes a main body including a distraction tab and a reduction foot; a secondary link pivotably mounted to the main body; a drive link coupled between the secondary link and the distraction aperture; a distraction actuator coupled to the drive link and structured to move the main body relative the secondary link; a proximal anchor pivotably coupled to the secondary link and including a proximal anchor foot configured to engage a proximal pedicle screw; a distal anchor pivotably coupled to the main body and including a distal anchor foot configured to engage a distal pedicle screw; and a reduction actuator engaged between the reduction foot and the distal anchor to move the distal anchor foot relative to the main body.

Another implementation relates to a method that includes seating a proximal anchor within a saddle of a proximal pedicle screw; coupling a proximal locking cap to the proximal pedicle screw; seating a distal anchor within a saddle of a distal pedicle screw; coupling a distal locking cap to the distal pedicle screw; inserting a proximal anchor thread of the proximal anchor into a proximal bar aperture provided in a proximal bar; coupling a proximal poly nut to the proximal anchor thread; rotating a distraction nut to expand a distractor by pulling the distal anchor and the proximal anchor apart; and rotating a reduction screw to move the distal anchor relative to a main body.

This summary is illustrative only and is not intended to be in any way limiting. Other aspects, inventive features, and advantages of the devices or processes described herein will become apparent in the detailed description set forth herein, taken in conjunction with the accompanying figures, wherein like reference numerals refer to like elements.

BRIEF DESCRIPTION OF DRAWINGS

The device is explained in even greater detail in the following drawings. The drawings are merely exemplary and certain features may be used singularly or in combination with other features. The drawings are not necessarily drawn to scale.

FIGS. 35-45 are perspective views of the pedicle screw distractor and reduction instrument of FIG. 34 during use, according to some implementations.

DETAILED DESCRIPTION

Figure 1:
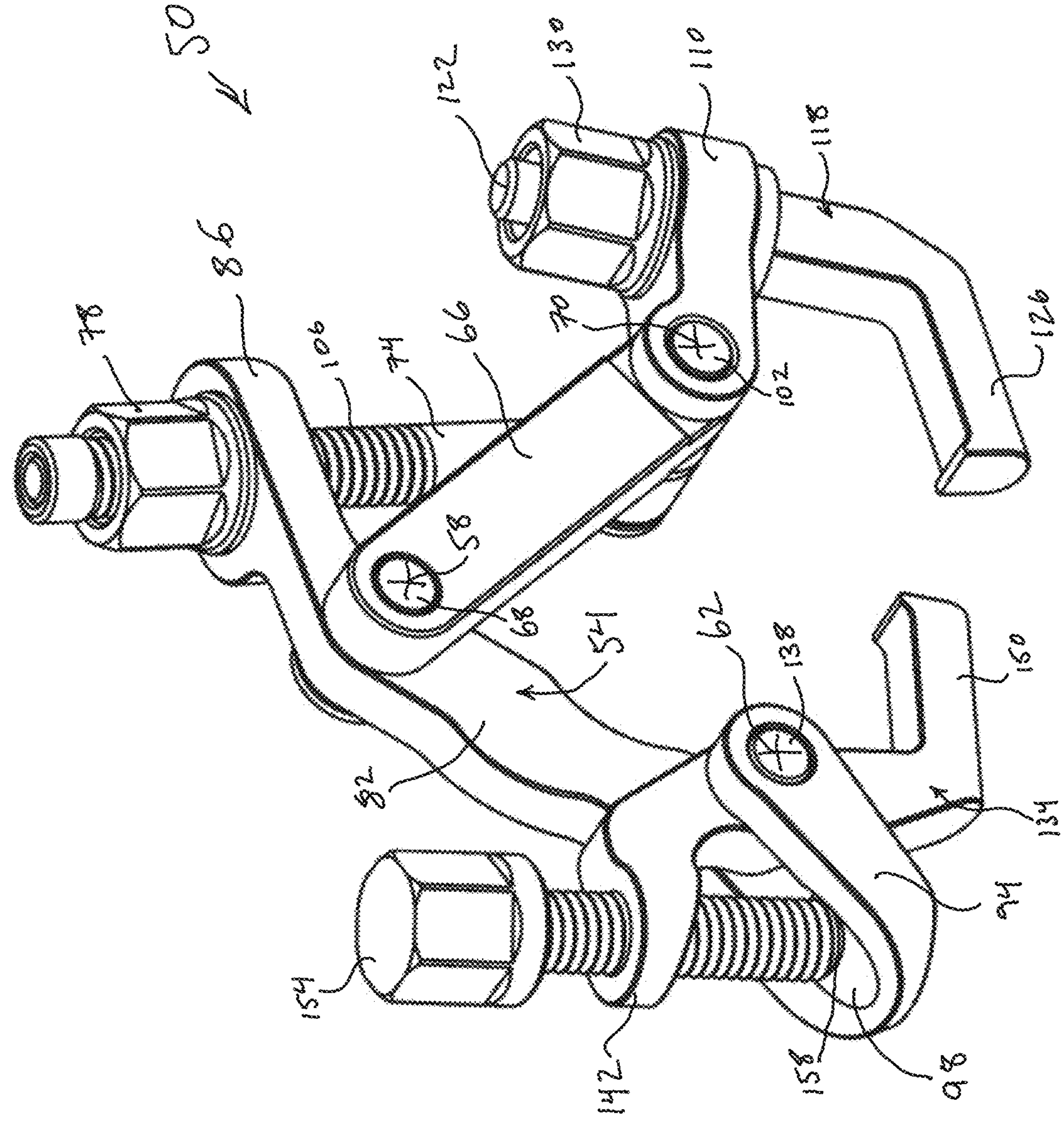
FIG. 1 is a perspective view of a pedicle screw distractor and reduction instrument, according to some implementations.
Figure 2:
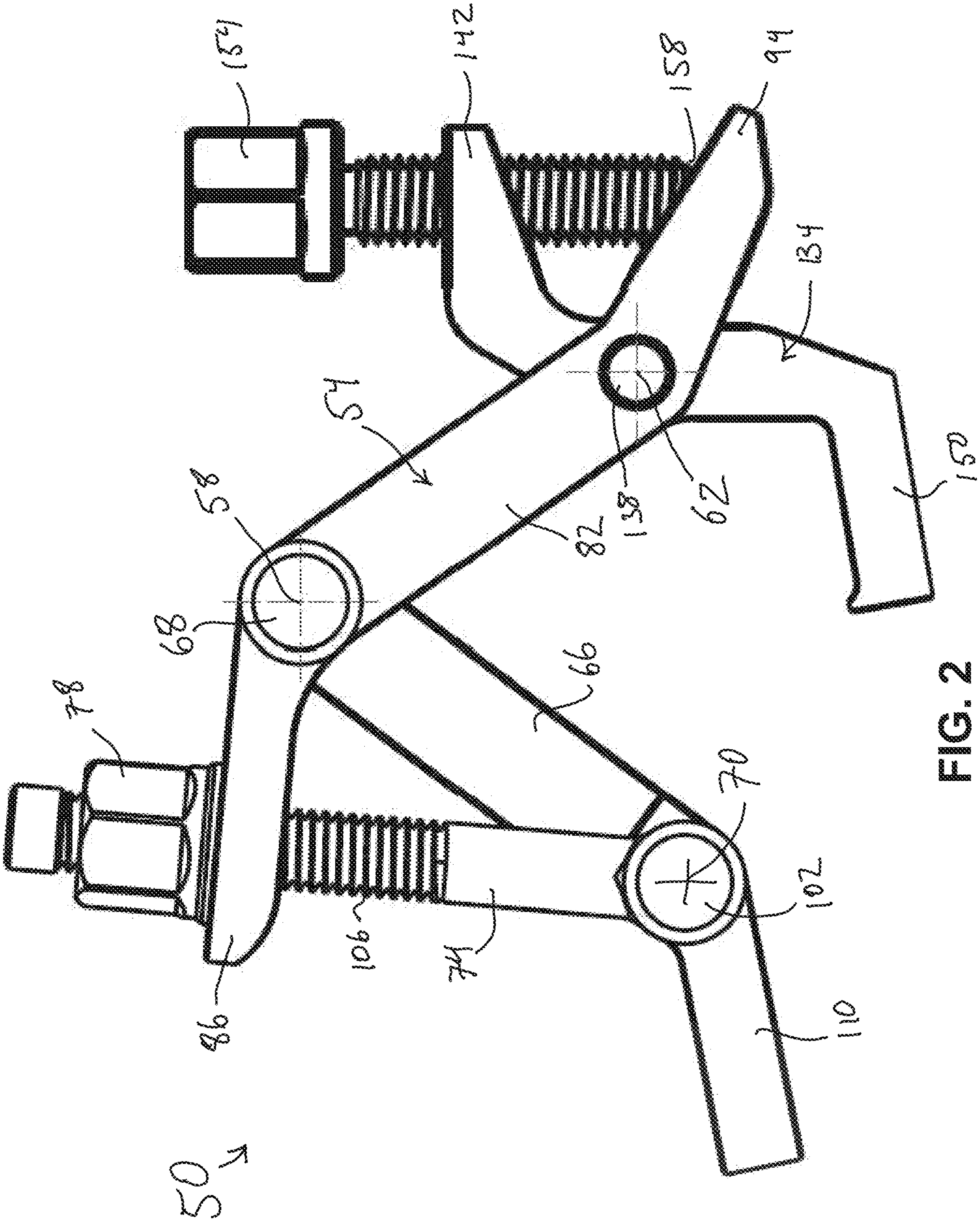
FIG. 2 is a front view of the pedicle screw distractor and reduction instrument of FIG. 1, according to some implementations.
Figure 3:
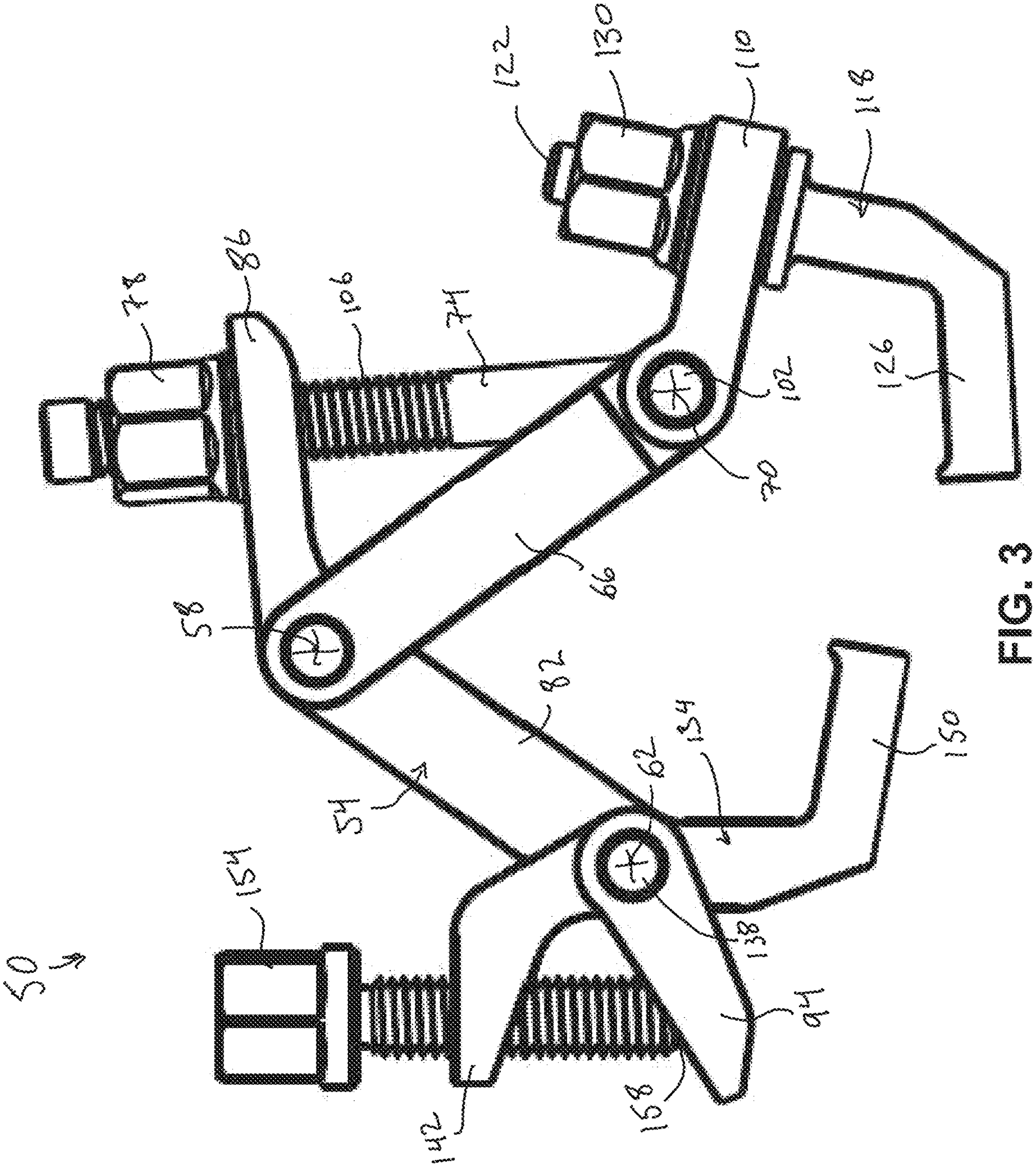
FIG. 3 is a rear view of the pedicle screw distractor and reduction instrument of FIG. 1, according to some implementations.
Figure 4:
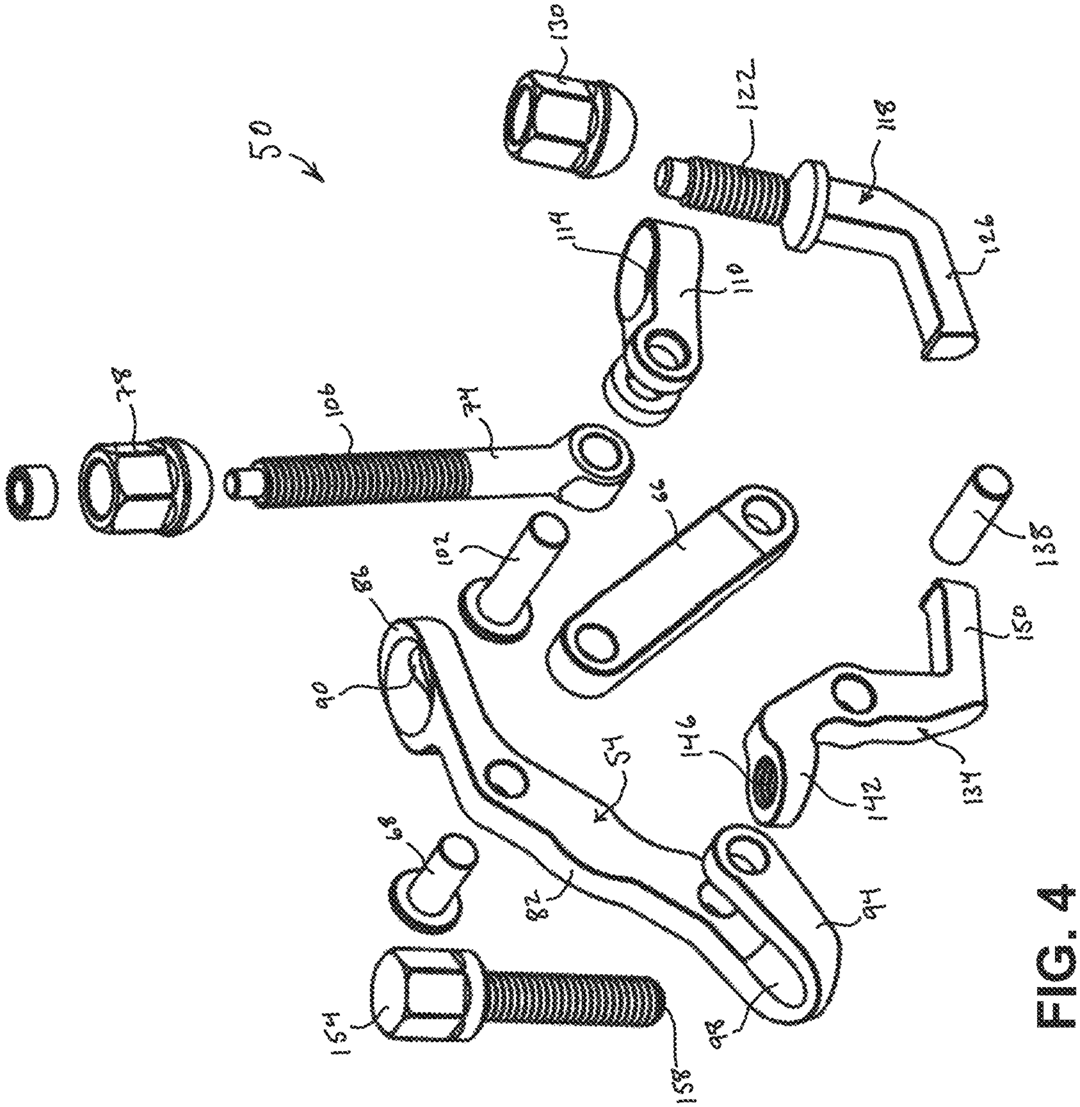
FIG. 4 is an exploded view of the pedicle screw distractor and reduction instrument of FIG. 1, according to some implementations.

Following below are more detailed descriptions of concepts related to, and implementations of, methods, apparatuses, and systems for pedicle screw distractor/reduction. Before turning to the figures, which illustrate certain exemplary embodiments in detail, it should be understood that the present disclosure is not limited to the details or methodology set forth in the description or illustrated in the figures. It should also be understood that the terminology used herein is for the purpose of description only and should not be regarded as limiting.

Referring to the figures generally, the various embodiments disclosed herein relate to systems, apparatuses, and methods for a pedicle screw distractor and reduction instrument that can be used to correct various cervical spondylosis and curvatures. The pedicle screw distractor and reduction instrument allows for a universal fit on standard pedicle screws and provides an improved range of motion allowing the instrument to reach and reduce high grade spondylolisthesis.

Generally, the pedicle screw distractor and reduction instrument includes a distal anchor sized and configured to couple to a first poly-axial pedicle screw. The distal anchor is coupled to a main body of the distractor. A reduction screw coupled between the distal anchor and the main body and directs movement therebetween. The main body is coupled to a proximal anchor via a secondary linkage and a proximal bar. The proximal anchor extends through an opening in the proximal bar. A proximal poly nut is used to couple and fix the location of the proximal anchor with respect to the proximal bar. The proximal anchor is sized and configured to couple to a second poly-axial bone screw. The proximal and distal anchors are sized and configured to universally couple to standard poly-axial pedicle screws (e.g., proximal and distal anchors can be received within the saddle portion of a standard 5.5 mm implants/pedicle screws, with the locking screw fixing the anchor within the pedicle screw head). It is also contemplated that the anchors described herein can be used in conjunction with monoaxial and uni-planar pedicle screws.

Rotation of a distraction nut coupled to the main body drives movement between the main body and the proximal anchor. A drive linkage extends from the secondary linkage/proximal bar to an opening in the main body. For example, secondary linkage and proximal bar are coupled at a pivoting connection point. The lower end of the drive linkage is coupled at the pivoting connection point. The upper end of the drive linkage extends through an opening in the main body. As the distraction nut is rotated the drive linkage moves (e.g., proximally) within the opening in the main body, drawing the proximal bar and proximal anchor (at the connection point) in the corresponding (e.g., proximal) direction. This results in a corresponding lifting and reducing the proximal pedicle screw/vertebral body.

As shown in FIGS. 1-4, a pedicle screw distractor and reduction instrument 50 includes a main body 54 defining a first pivot axis 58 and a second pivot axis 62, a secondary link 66 pivotably coupled to the first pivot axis 58 of the main body 54 with a first pin 68 and defining a third pivot axis 70, and a drive link 74 coupled between the main body 54 and the third pivot axis 70. The drive link 74 is actuatable to move the secondary link 66 relative to the main body 54 between a maximum expansion position (see FIG. 6) and a minimum expansion position (see FIG. 7). A distraction actuator in the form of a distraction nut 78 is threaded to the drive link 74 and provides actuation of the drive link 74.

The main body 54 includes a central bar 82 extending between the first pivot axis 58 and the second pivot axis 62. A distraction tab 86 extends from the central bar 82 adjacent the first pivot axis 58 and is arranged at an oblique angle relative to the central bar 82 and defines a distraction aperture 90 (see FIG. 4) sized to receive the drive link 74. In some implementations, the distraction aperture 90 includes a chamfer or other centering feature sized to engage and center the distraction nut 78 within the distraction aperture 90. In some implementations, the central bar 82 defines a longitudinal axis intersecting the first pivot axis 58 and the second pivot axis 62, and the distraction tab 86 defines a longitudinal axis arranged at a distraction tab angle. In some implementations, the distraction tab angle is 130 degrees. In some implementations, the distraction angle is 100 degrees to 150 degrees. A reduction foot 94 extends from the central bar 82 adjacent the second pivot axis 62 and is arranged at an oblique angle relative to the central bar 82 and defines a race 98. In some implementations, the race 98 includes a radially swept arc similar to a bearing race. In some implementations, the central bar 82 defines a longitudinal axis intersecting the first pivot axis 58 and the second pivot axis 62, and the reduction foot 94 defines a longitudinal axis arranged at a reduction foot angle. In some implementations, the reduction foot angle is 156.5 degrees. In some implementations, the distraction angle is 140 degrees to 170 degrees.

The secondary link 66 is connected to the drive link 74 at the third pivot axis 70 with a third pin 102. In some implementations, the third pin 102 is formed as a part of the drive link 74. in some implementations, the third pin 102 is separately formed and engaged with the drive link 74 and the secondary link 66 to provide relative rotation therebetween.

The drive link 74 is received through the distraction aperture 90 of the distraction tab 86 and is connected to the third pin 102 at the third pivot axis 70. The drive link 74 includes distraction threads 106 that are engaged with the distraction nut 78 so that threading the distraction nut 78 along the distraction threads 106 actuates the secondary link 66 relative to the main body 54 between the maximum expansion position and the minimum expansion position.

A proximal bar 110 is connected to the secondary link 66 and the drive link 74 at the third pivot axis 70 by the third pin 102 and is rotatable relative to the secondary link 66 and the drive link 74. The proximal bar 110 defines a proximal bar aperture 114 (see FIG. 4) that includes a centering feature in the form of a chamfer or other concave surface. In some implementations, the centering feature of the proximal bar aperture 114 includes a semi-circular surface. In some implementations, the proximal bar 110 can freely rotate about the third pivot axis 70.

A proximal anchor 118 is received through the proximal bar aperture 114 and includes a proximal anchor thread 122 (see FIG. 4), and a proximal anchor foot 126 that is shaped to engage a pedicle screw. A poly nut 130 is threadingly engaged with the proximal anchor thread 122 to hold the proximal anchor 118 within the proximal bar aperture 114. The centering feature of the proximal bar aperture 114 provides a range of radial displacement of the proximal anchor 118 relative to the proximal bar 110. In some implementations, the proximal anchor 118 can move within the proximal bar aperture 114 from 0 degrees to 15 degrees from center.

A distal anchor 134 is pivotally connected to the main body 54 at the second pivot axis 62 by a second pin 138. The distal anchor 134 includes a distal anchor tab 142 defining a distal anchor actuator in the form of a distal anchor threaded aperture 146 (see FIG. 4) and a distal anchor foot 150. A reduction screw 154 is sized to threadingly engage the aperture 146 and defines a cam follower head 158 shaped to slidingly engage the race 98 of the reduction foot 94. The reduction screw 154 is actuatable relative to the distal anchor 134 between a maximum reduction position (see FIG. 9A) and a minimum reduction position (see FIG. 9C).

Figure 5:
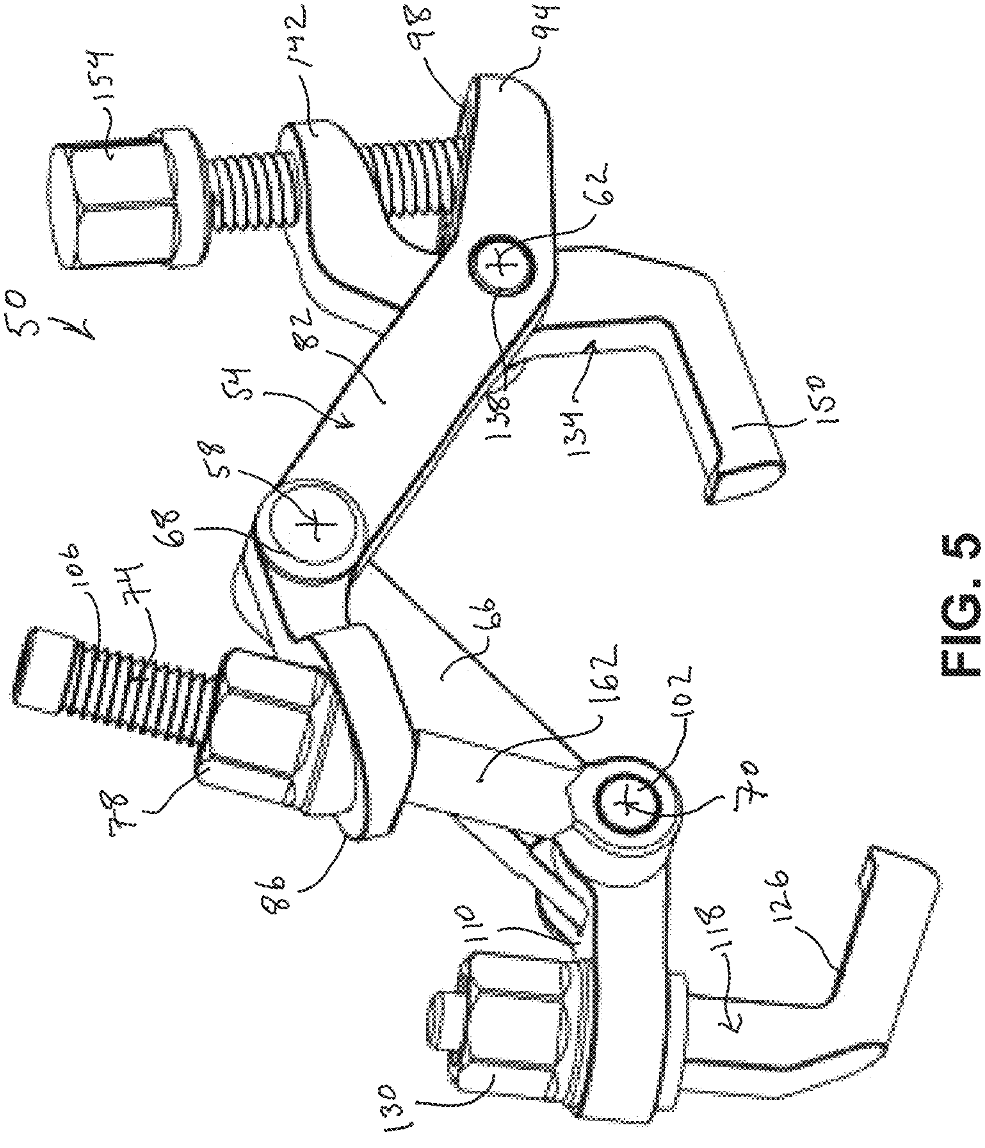
FIG. 5 is a rear view of the pedicle screw distractor and reduction instrument of FIG. 1 including a biasing element, according to some implementations.
Figure 6:
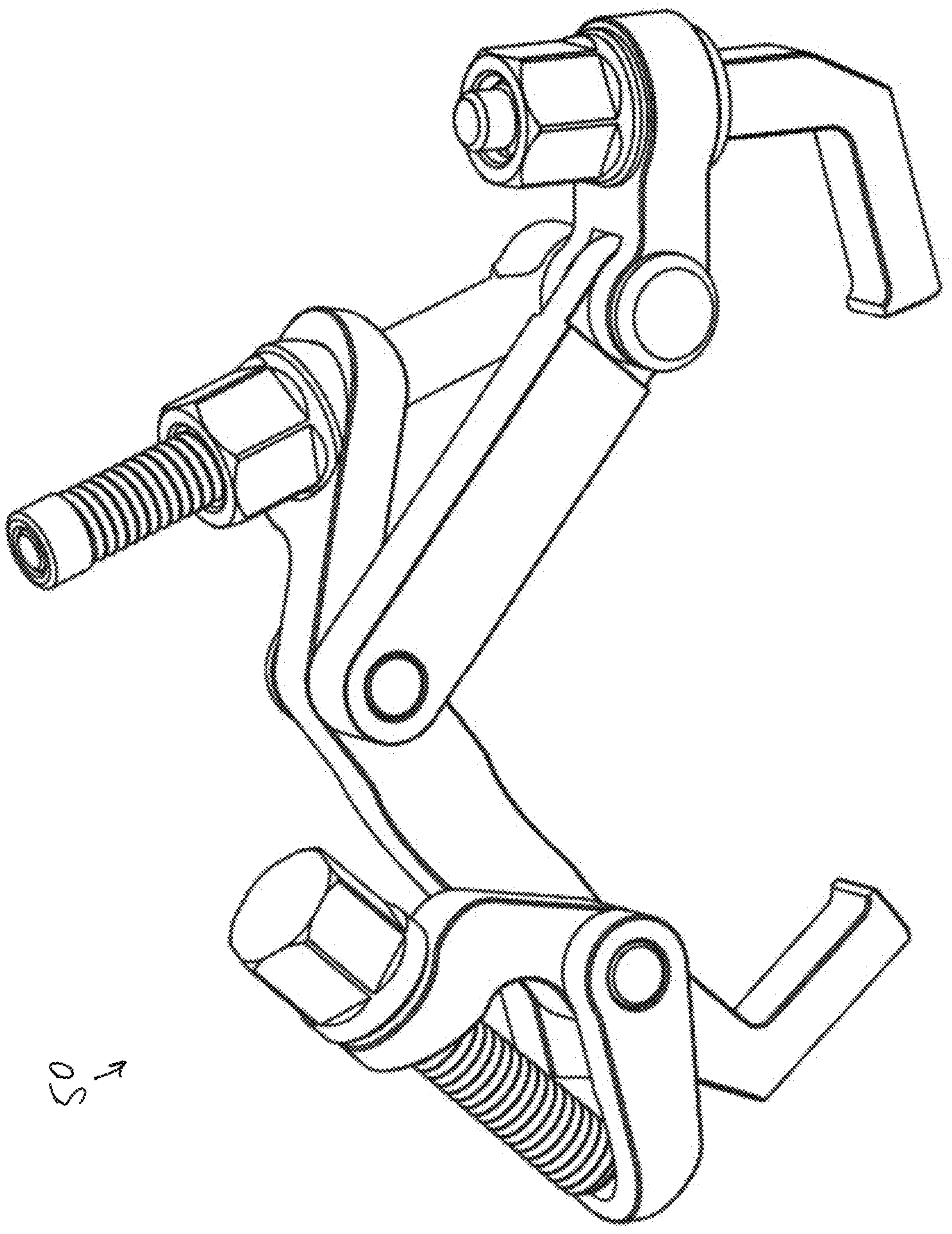
FIG. 6 is a perspective view of the pedicle screw distractor and reduction instrument of FIG. 1 in a maximum expansion position, according to some implementations.
Figure 7:
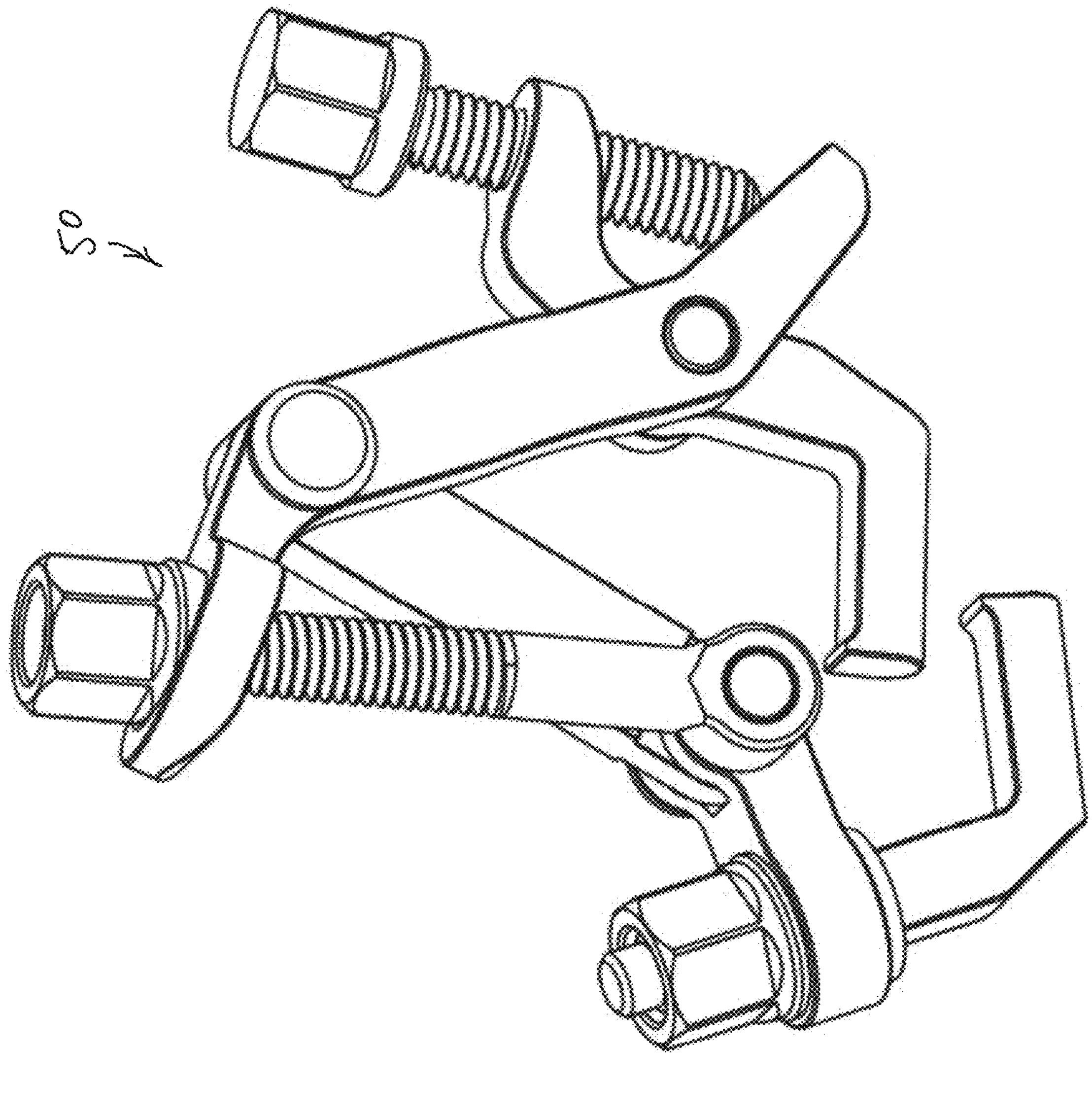
FIG. 7 is a perspective view of the pedicle screw distractor and reduction instrument of FIG. 1 in a minimum expansion position, according to some implementations.

As shown in FIG. 5, in some implementations, the pedicle screw distractor and reduction instrument 50 includes a biasing element in the form of a spring 162 arranged to bias the distraction tab 86 of the main body 54 away from the third pivot axis 70 and toward the minimum expansion position. FIG. 6 shows the pedicle screw distractor and reduction instrument 50 in the maximum expansion position according to some implementations. FIG. 7 shows the pedicle screw distractor and reduction instrument 50 in the minimum expansion position according to some implementations.

Figure 8:
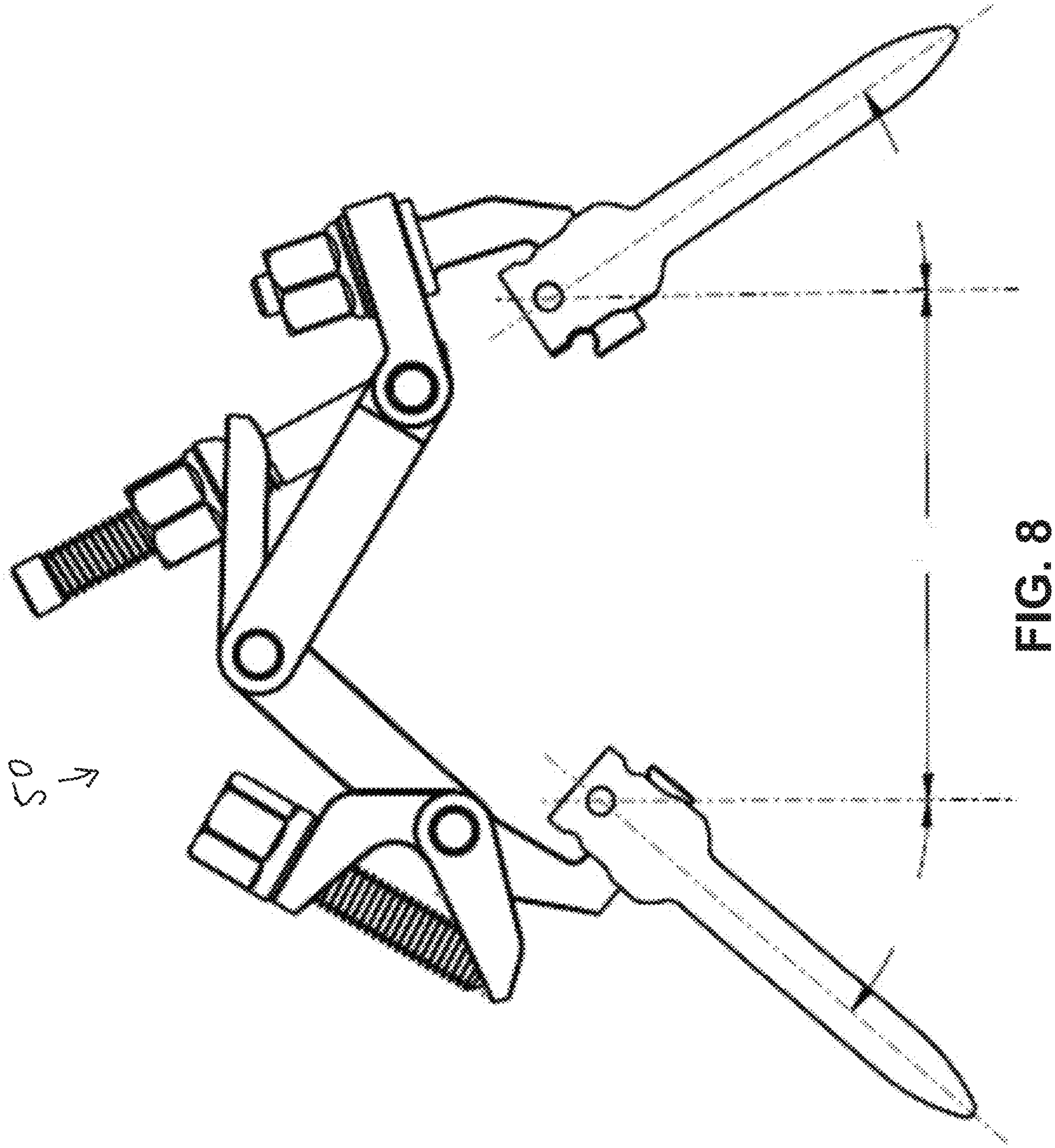
FIG. 8 is a perspective view of the pedicle screw distractor and reduction instrument of FIG. 1 including pedicle screws, according to some implementations.

As shown in FIG. 8, in some implementations, the maximum expansion position provides 50 mm of distance between rotational axis points of two pedicle screws during use. Additionally, the arrangement of the proximal anchor 118 provides a ±15 degree freedom of movement of the proximal pedicle screw and the distal anchor 134 provides a ±35 degree freedom of movement of the distal pedicle screw.

Figure 9B:
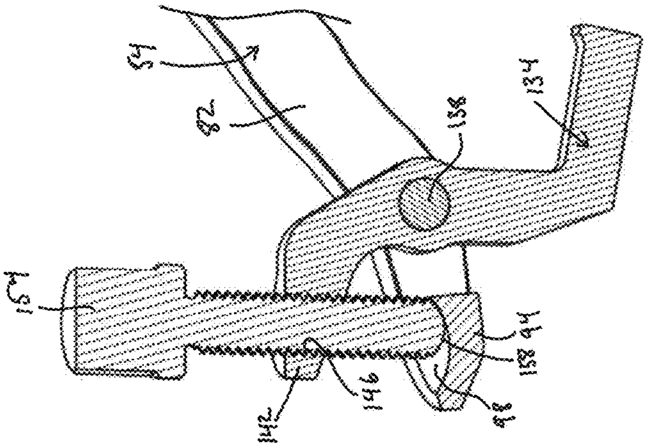
FIGS. 9A-9C are sectional views of a reduction screw of the pedicle screw distractor and reduction instrument, according to some implementations.
Figure 9C:
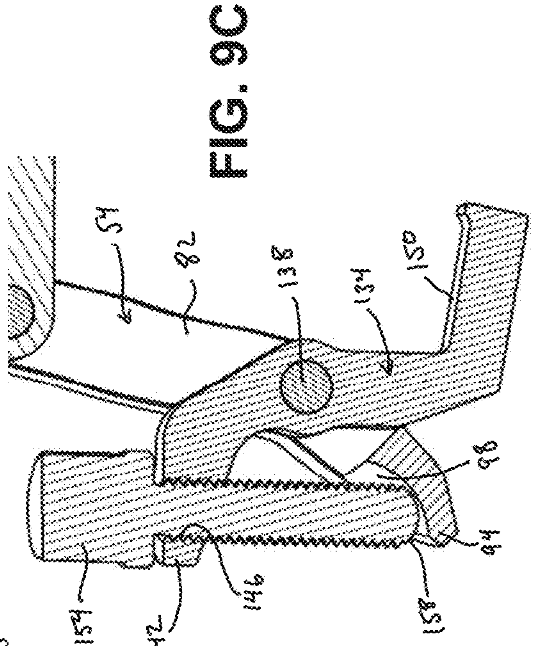
Figure 9A:
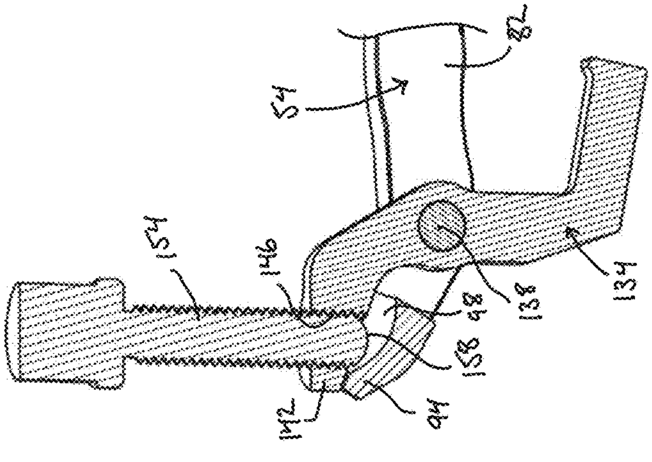

As shown in FIGS. 9A-9C, the reduction screw 154 can be threaded through the aperture 146 to actuate the distal anchor 134 relative to the main body 54. During actuation, the cam follower head 158 rides along the race 98 of the reduction foot 94. In some implementations, the distal anchor 134 is movable along 50 degrees of travel.

A method of using the pedicle screw distractor and reduction instrument 50 is described herein in reference to FIGS. 10-14. While listed in a particular order, it is contemplated that the order of steps provided here is not limited and steps may occur in different order.

Figure 10:
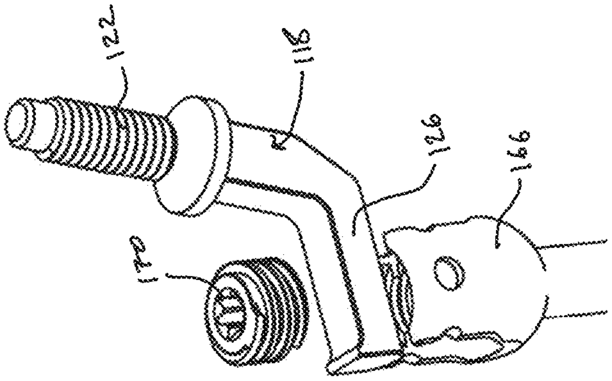
FIG. 10 is a perspective view of a proximal anchor, according to some implementations.

As shown in FIG. 10, the proximal anchor 118 is seated within a U-shaped saddle of a proximal pedicle screw 166. A proximal locking cap 170 is coupled to the head of the proximal pedicle screw 166 and torqued according to manufactures recommendation. In some implementations, a cross-sectional shape of the proximal anchor 118 does not correspond to the shape of the channel provided in the head of the proximal pedicle screw 166. As such, the proximal anchor 118 may rotated within the channel until the proximal locking cap 170 is secured.

Figure 11:
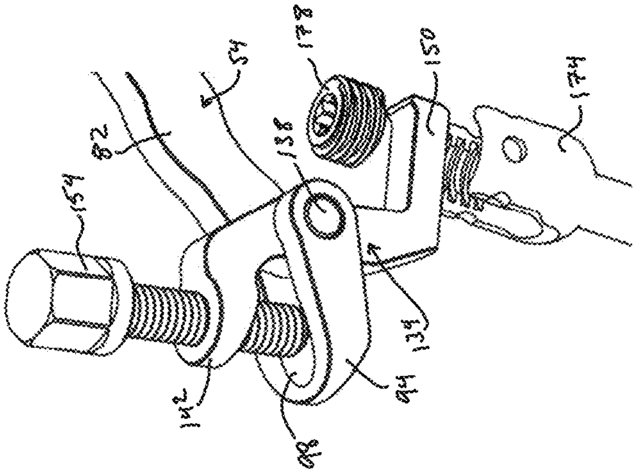
FIG. 11 is a perspective view of a distal anchor, according to some implementations.

As shown in FIG. 11, the distal anchor 134 is seated within a U-shaped saddle of a distal pedicle screw 174. A distal locking cap 178 is coupled to the head of the distal pedicle screw 174 and torqued according to manufactures recommendation. In some implementations, a cross-sectional shape of the distal anchor foot 150 corresponds to a cross-sectional shape of the channel provided in the head of the distal pedicle screw 174. As such, the distal anchor 134 does not rotate with regard to the distal pedicle screw 174.

Figure 12:
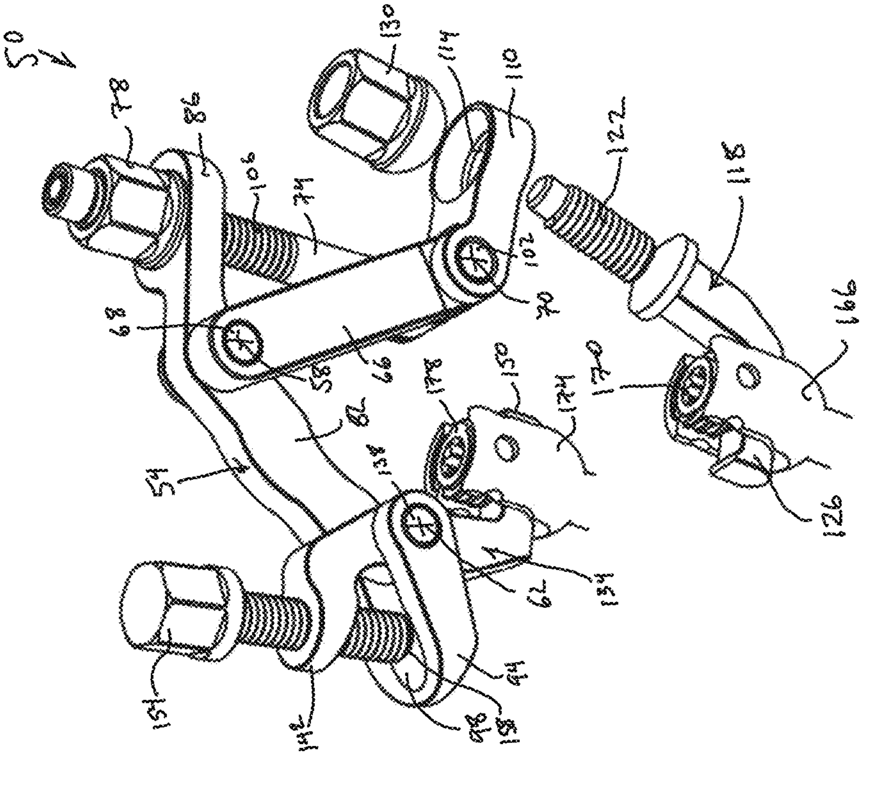
FIG. 12 is a perspective view of the pedicle screw distractor and reduction instrument of FIG. 1, according to some implementations.

As shown in FIG. 12, the proximal anchor thread 122 of the proximal anchor 118 is inserted into the proximal bar aperture 114 provided in the proximal bar 110. The proximal poly nut 130 is coupled to the proximal anchor thread 122.

Figure 13:
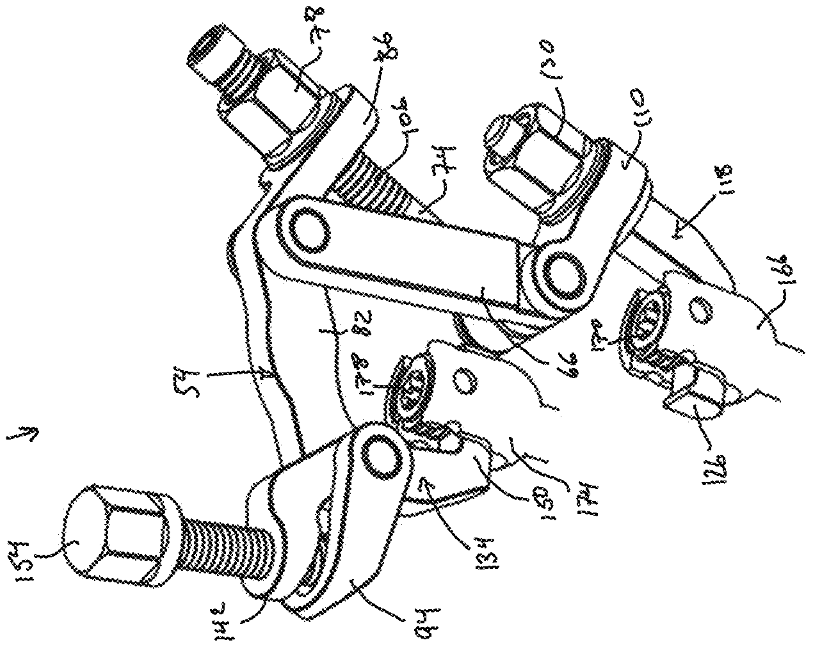
FIG. 13 is a perspective view of the pedicle screw distractor and reduction instrument of FIG. 1, according to some implementations.

As shown in FIG. 13, the poly nut 130 allows for misalignment of proximal anchor 118 (e.g., up to 30°, that is up to 15° per side). The poly nut 130 can be left loose during distraction to allow for addition poly motion at the proximal joint. The poly nut 130 can be tightened to reduce degrees of freedom at the proximal poly joint. The poly nut 130 can be tightened or loosened during distraction and reduction as needed.

Figure 14:
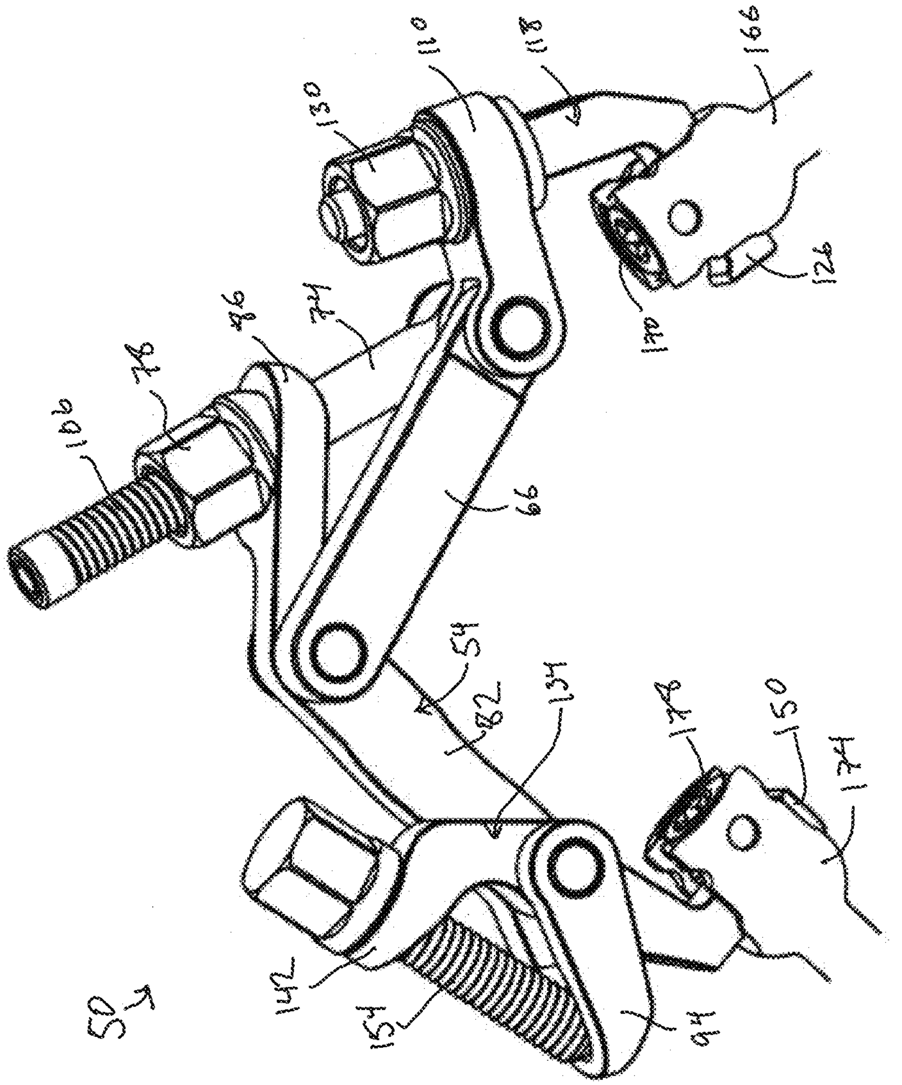
FIG. 14 is a perspective view of the pedicle screw distractor and reduction instrument of FIG. 1, according to some implementations.

As shown in FIG. 14, the distraction nut 78 is rotated to expands distractor by pulling the distal anchor 134 and the proximal anchor 118 apart. The distraction nut 78 and reduction screw 154 are used in conjunction to achieve the desired distraction. Slow distraction allows for slow stretching of soft connective tissue and helps align pedicle screw rod slots.

The reduction screw 154 is used to lift and reduce spondylolisthesis. The reduction screw 154 and distraction nut 78 are used in conjunction to achieve the appropriate amount of reduction. Slow reduction allows for slow stretching of soft connective tissue and helps align pedicle screw rod slots.

The reduction screw 154 at maximum elevation (as shown in FIG. 14) provides a hard stop at maximum elevation. The reduction screw 154 can also be removed for cleaning as needed.

The distraction nut 78 at maximum actuation (as shown in FIG. 14) includes hard minimum and maximum stops. In some implementations, the distraction nut 78 cannot be removed.

The proximal poly nut 130 at maximum reduction (as shown in FIG. 14) the tertiary poly motion is completely reduced. In some implementations, the ploy nut 130 and proximal anchor 118 can be removed for cleaning.

The proximal bar rotation axis 70 remains free to pivot through entire range of motion. The pedicle screws 166, 174 implanted into vertebral body and soft connective tissue limits motion of joint.

In some examples the pedicle screw distractor and reduction instrument 50 is used in conjunction with one or more additional pedicle screw distractor/reduction instruments to effectively treat/reduce high grade spondylolisthesis (e.g., grade 5 spondylolisthesis).

Figure 17:
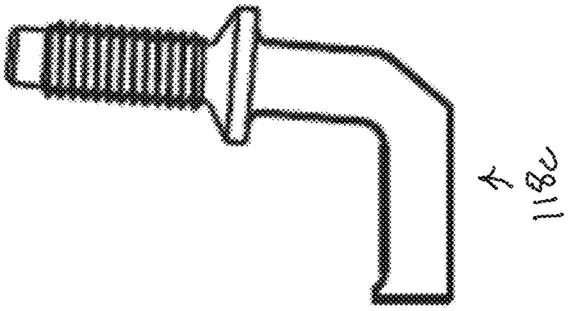
FIG. 17 is a perspective view of another example proximal anchor, according to some implementations.
Figure 16:
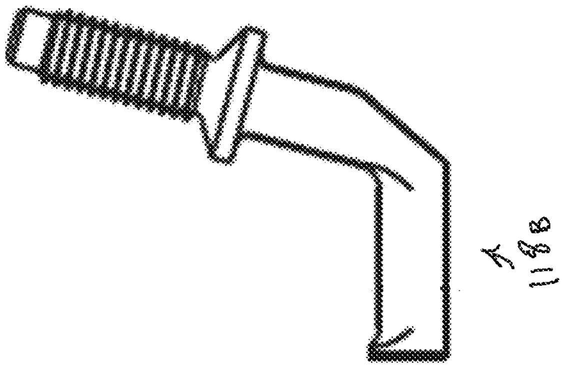
FIG. 16 is a perspective view of another example proximal anchor, according to some implementations.
Figure 15:
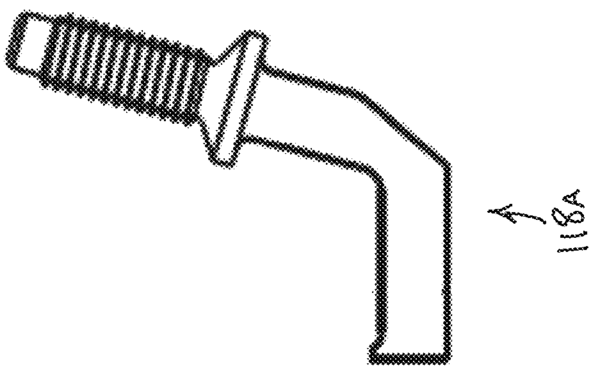
FIG. 15 is a perspective view of an example proximal anchor, according to some implementations.
Figure 20:
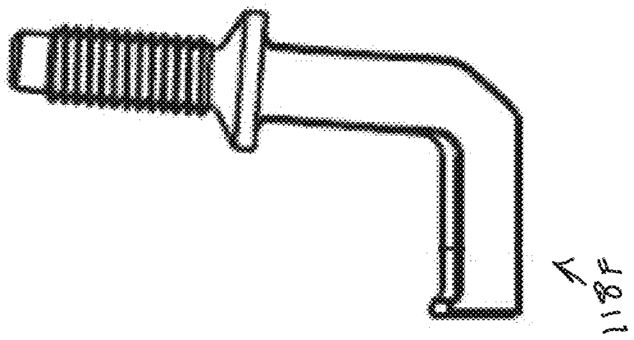
FIG. 20 is a perspective view of another example proximal anchor, according to some implementations.
Figure 19:
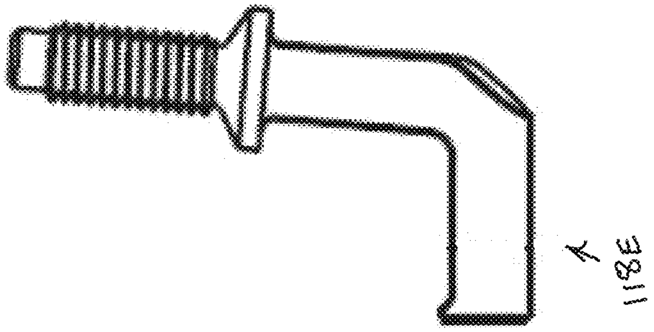
FIG. 19 is a perspective view of another example proximal anchor, according to some implementations.
Figure 18:
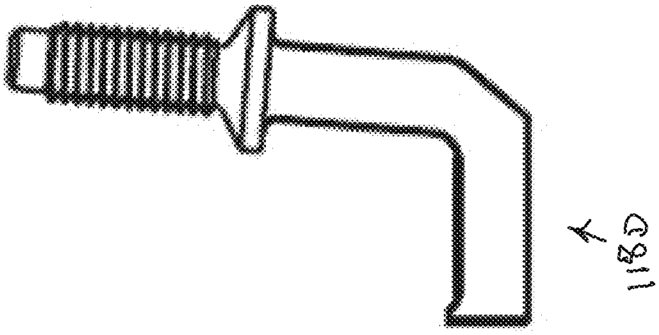
FIG. 18 is a perspective view of another example proximal anchor, according to some implementations.
Figure 22:
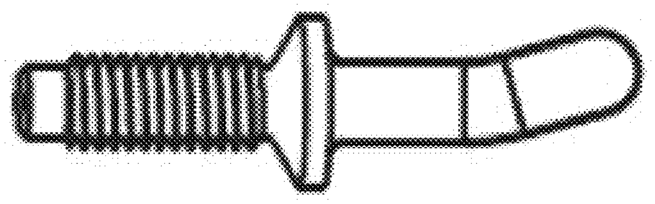
FIG. 22 is a rear view of the proximal anchor of FIG. 20, according to some implementations.
Figure 21:
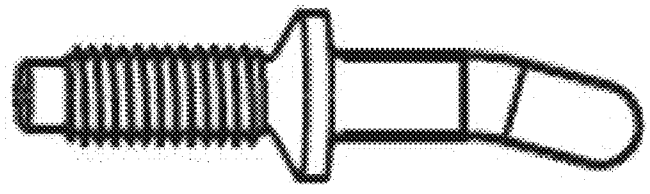
FIG. 21 is a rear view of the proximal anchor of FIG. 19, according to some implementations.
Figure 24:
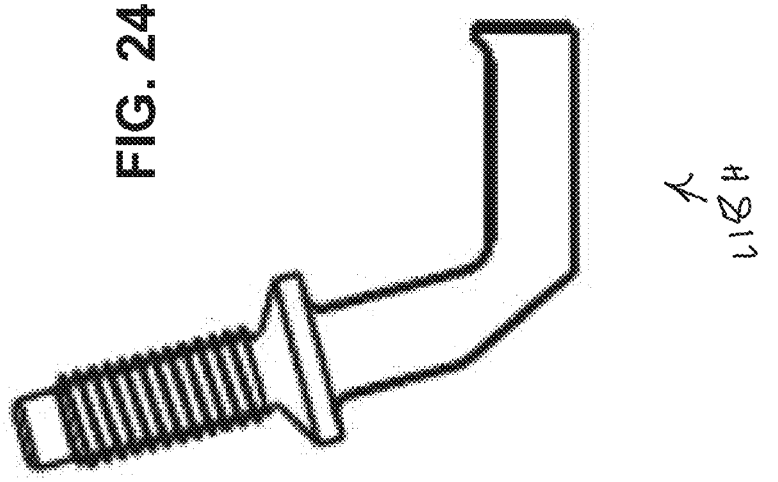
FIG. 24 is a perspective view of another example proximal anchor, according to some implementations.
Figure 23:
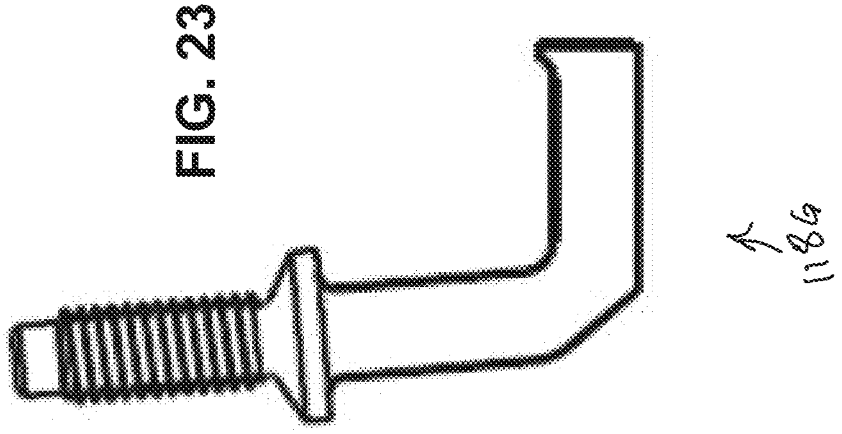
FIG. 23 is a perspective view of another example proximal anchor, according to some implementations.

As shown in FIGS. 15-17, the proximal anchor 118 can define a 105 degree angle between the proximal anchor foot 126 and the proximal anchor thread 122. The proximal anchor 118A includes a short U-shaped body. The proximal anchor 118B includes a short round body. The proximal anchor 118C includes a medium U-shaped body and may be the standard shape. As shown in FIGS. 18-20, the proximal anchor 118 can define a 95 degree angle between the proximal anchor foot 126 and the proximal anchor thread 122. The proximal anchor 118D includes a tall U-shaped body. The proximal anchor 118E includes a tall, U-shaped body with a left hand offset (see also FIG. 21). The proximal anchor 118F includes a tall, U-shaped body with a right hand offset (see also FIG. 22). FIG. 23 provides another example of a tall or extended proximal anchor 118G. FIG. 24 provides another example of a standard or short length proximal anchor 118H.

Figure 25:
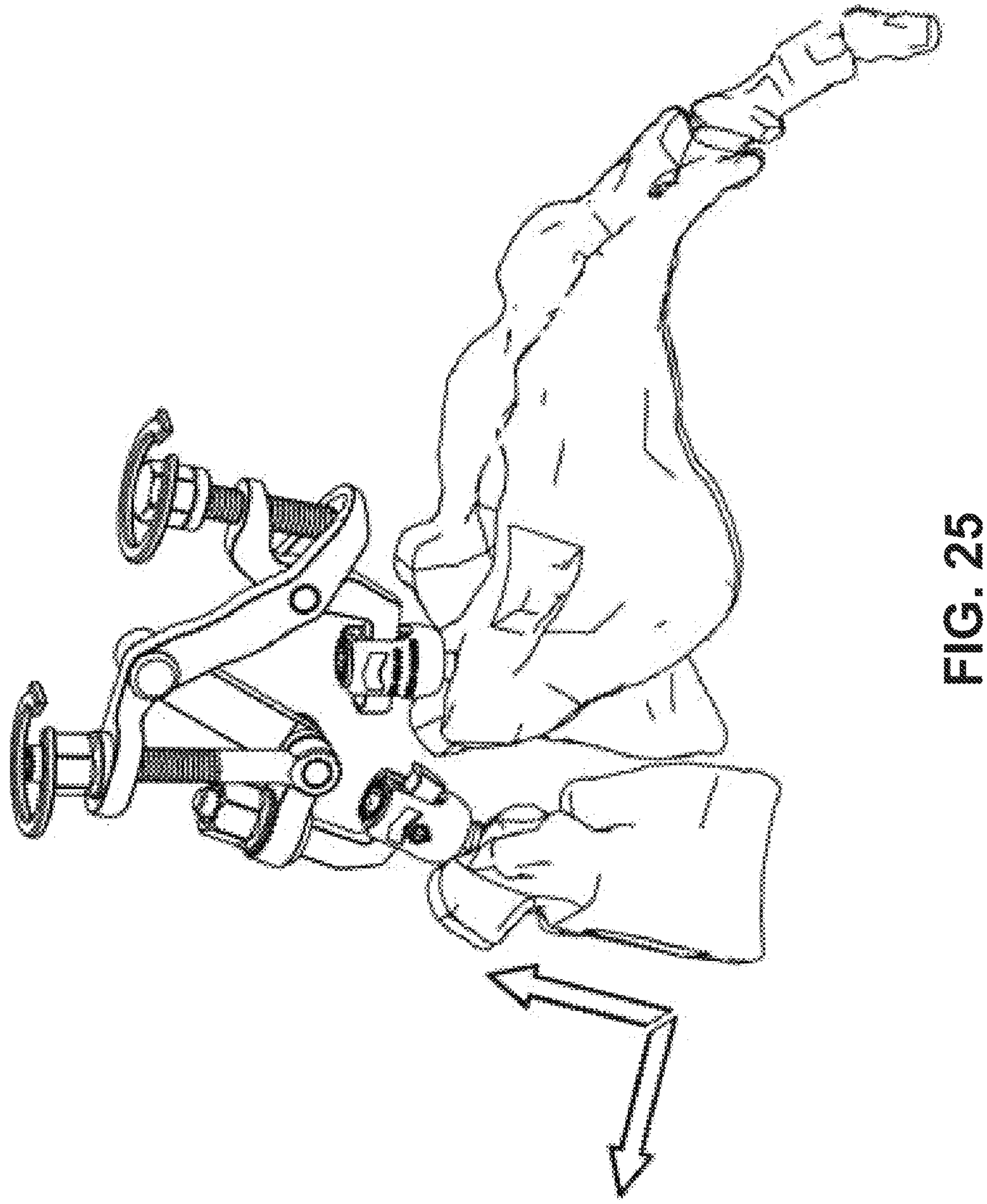
FIG. 25 is a perspective view of the pedicle screw distractor and reduction instrument of FIG. 1 in use, according to some implementations.
Figure 26:
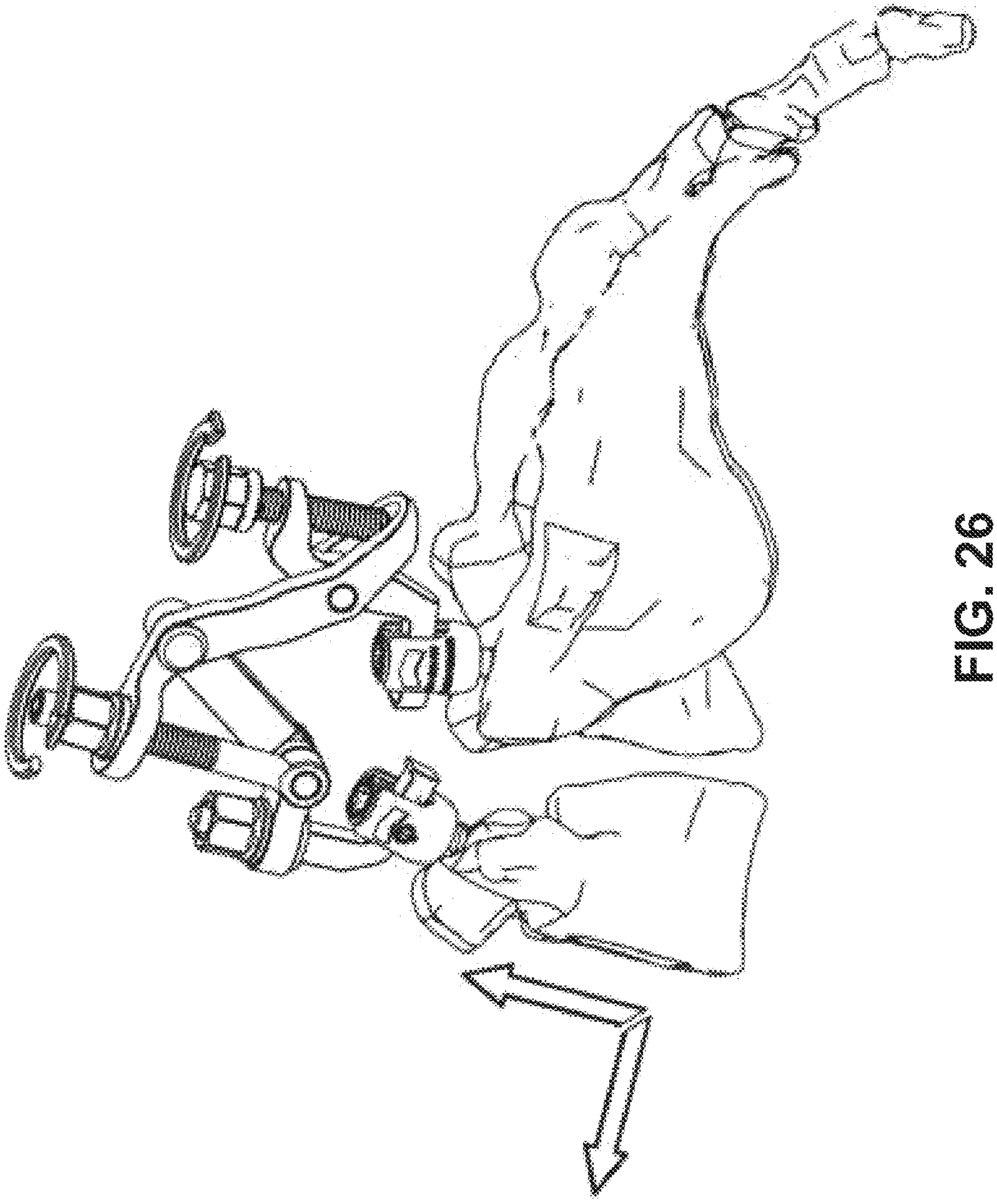
FIG. 26 is a perspective view of the pedicle screw distractor and reduction instrument of FIG. 1 in use, according to some implementations.
Figure 27:
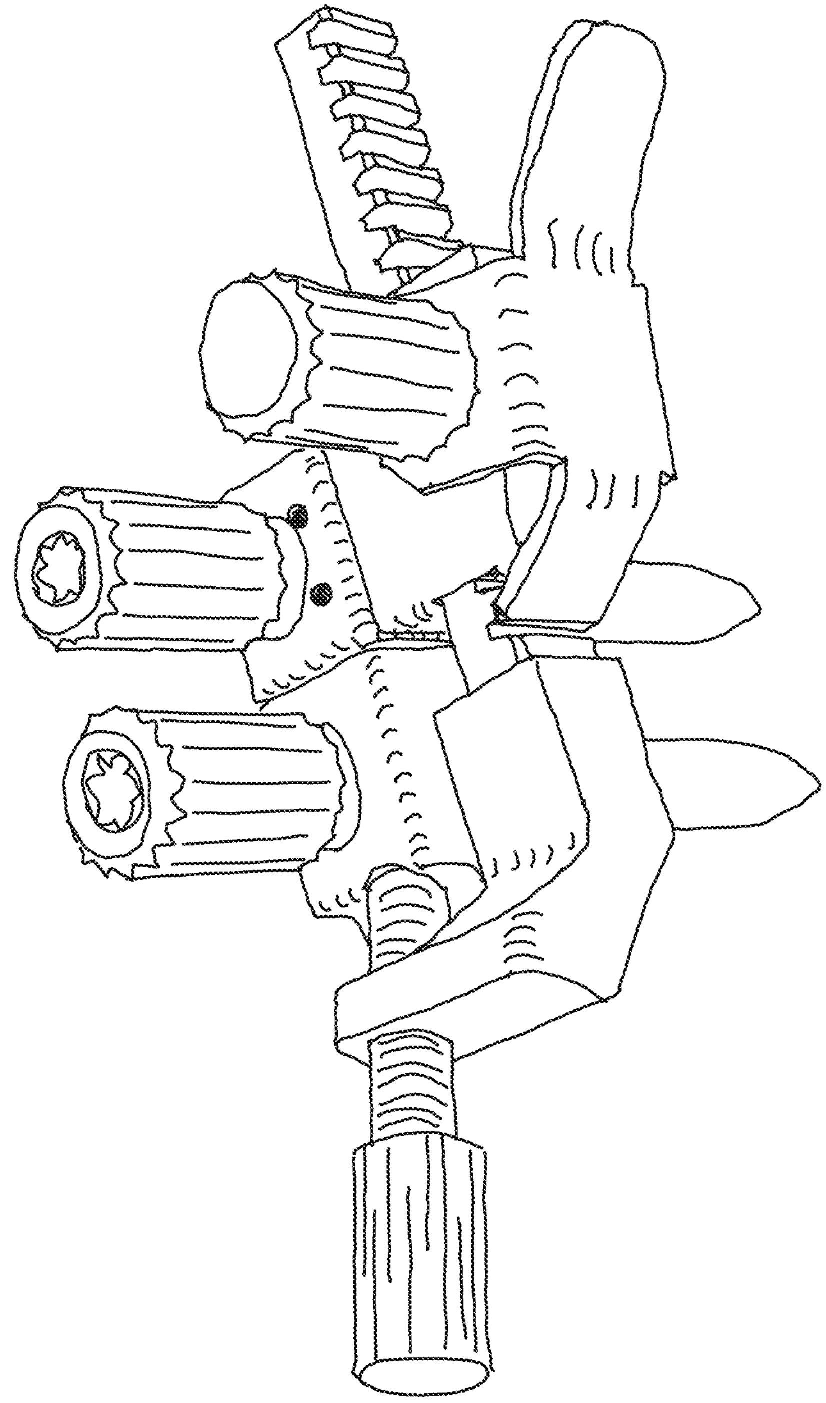
FIG. 27 is a perspective view of another pedicle screw distractor and reduction instrument, according to some implementations.
Figure 28:
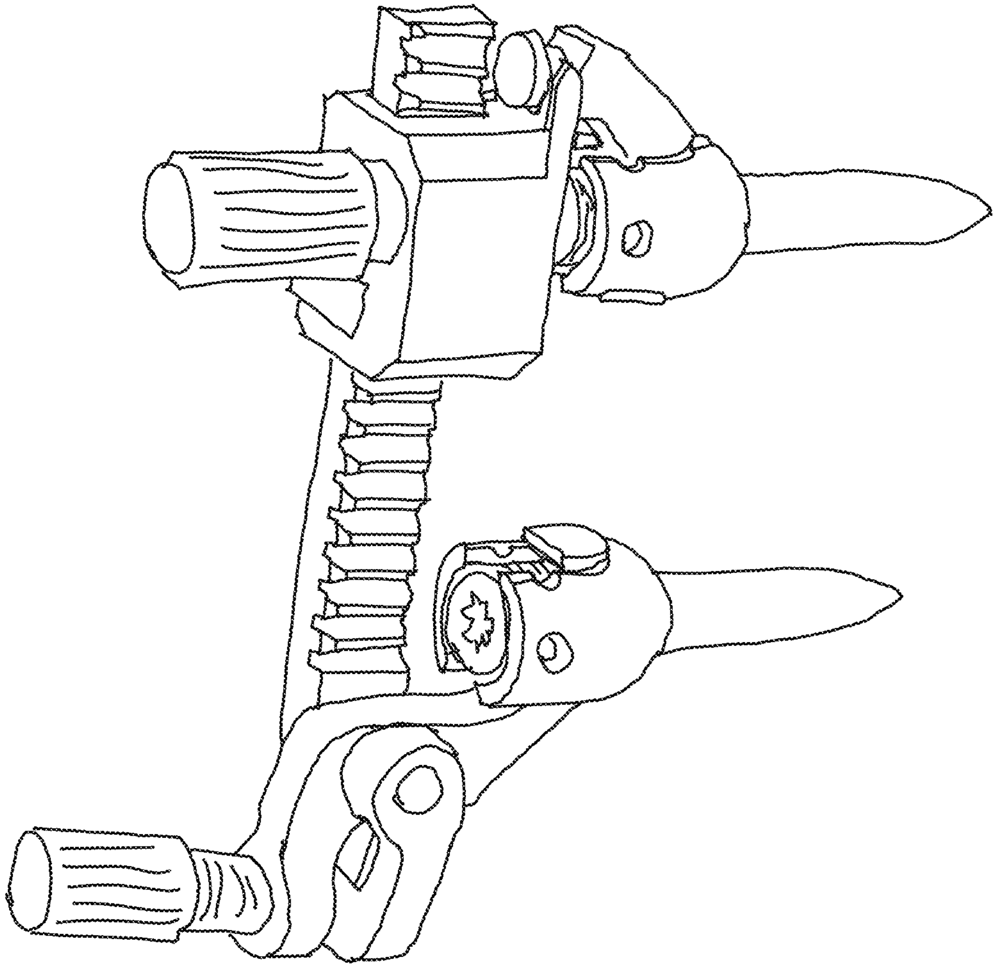
FIG. 28 is a perspective view of another pedicle screw distractor and reduction instrument, according to some implementations.
Figure 29:
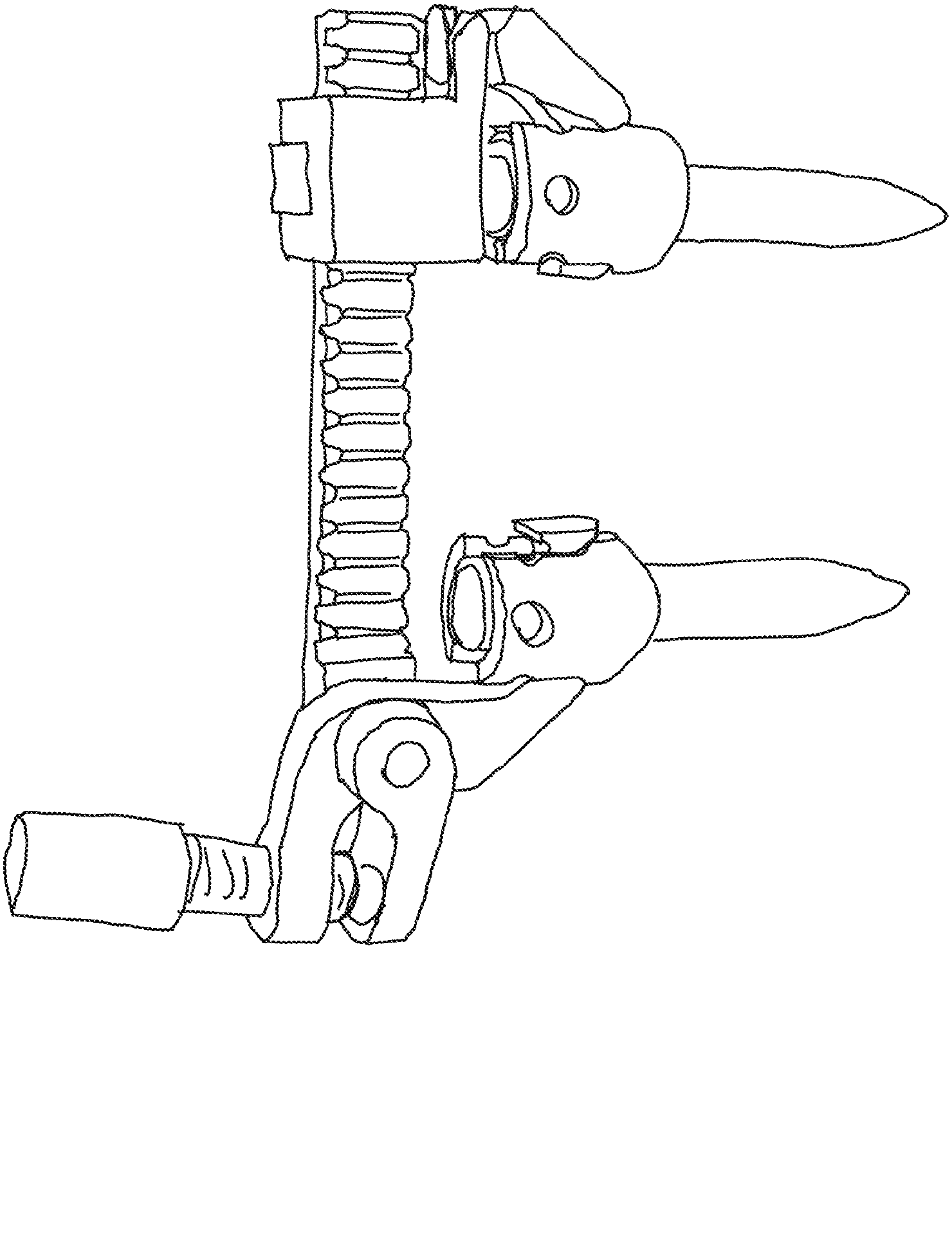
FIG. 29 is a perspective view of another pedicle screw distractor and reduction instrument, according to some implementations.
Figure 30:
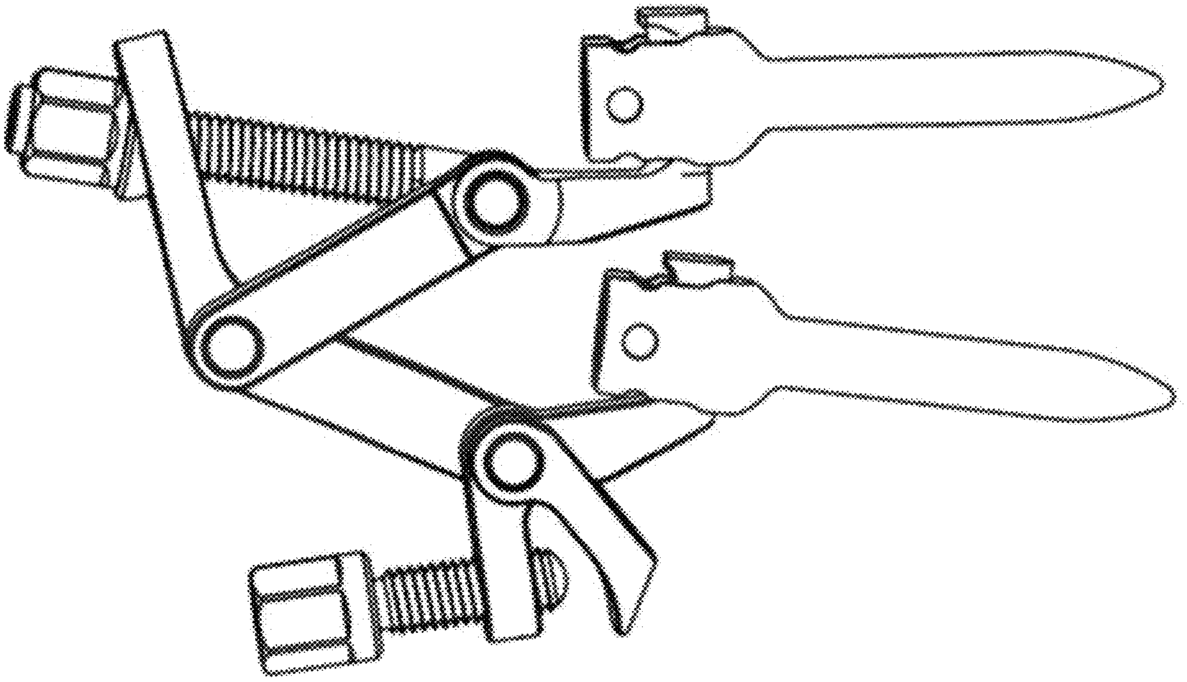
FIG. 30 is a perspective view of another pedicle screw distractor and reduction instrument, according to some implementations.

FIGS. 25 and 26 illustrate the pedicle screw distractor and reduction instrument 50 in use. FIGS. 27-30 illustrate alternative implementations of the pedicle screw distractor and reduction instrument 50.

Figure 31:
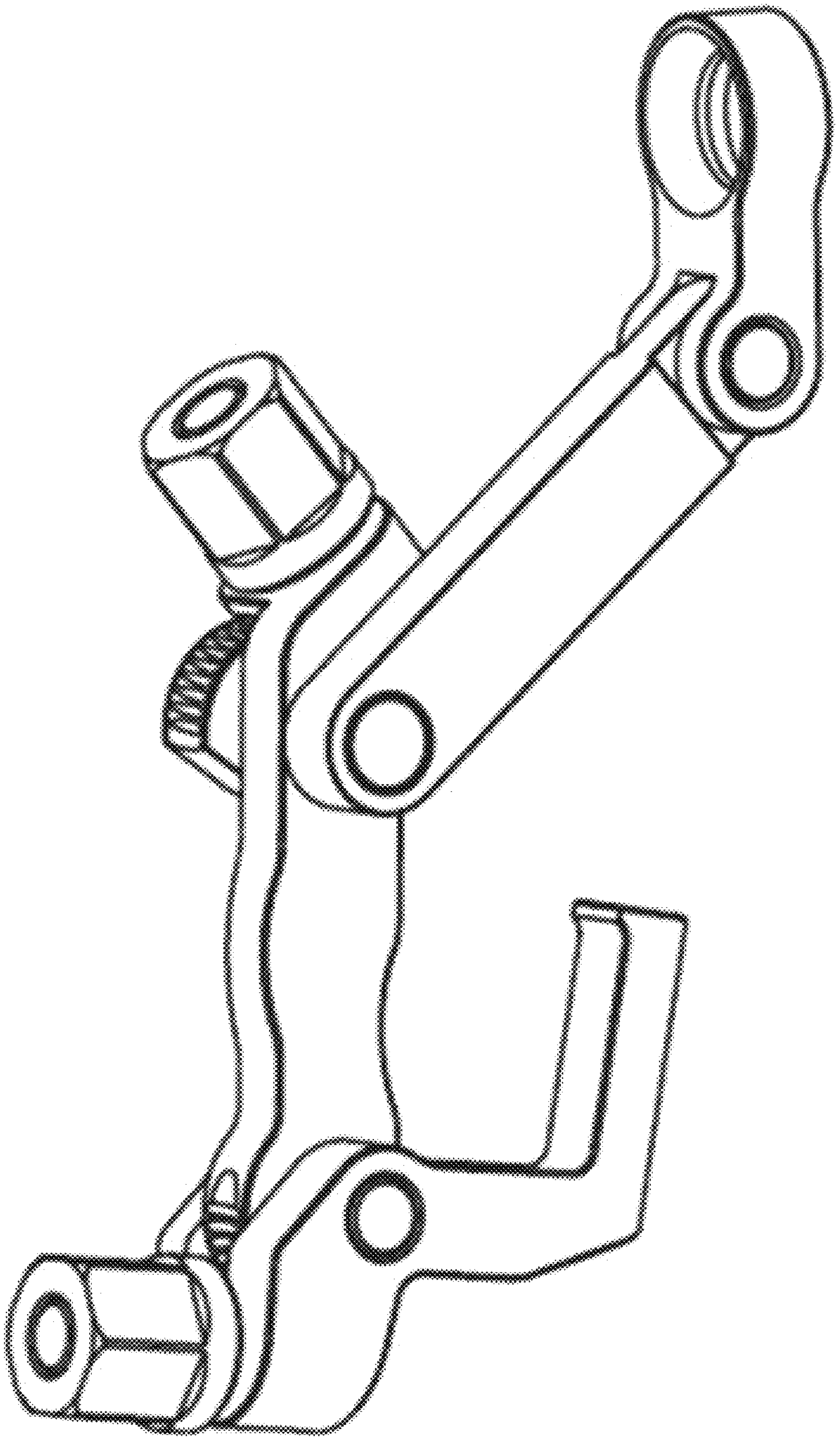
FIG. 31 is a perspective view of another pedicle screw distractor and reduction instrument, according to some implementations.
Figure 32:
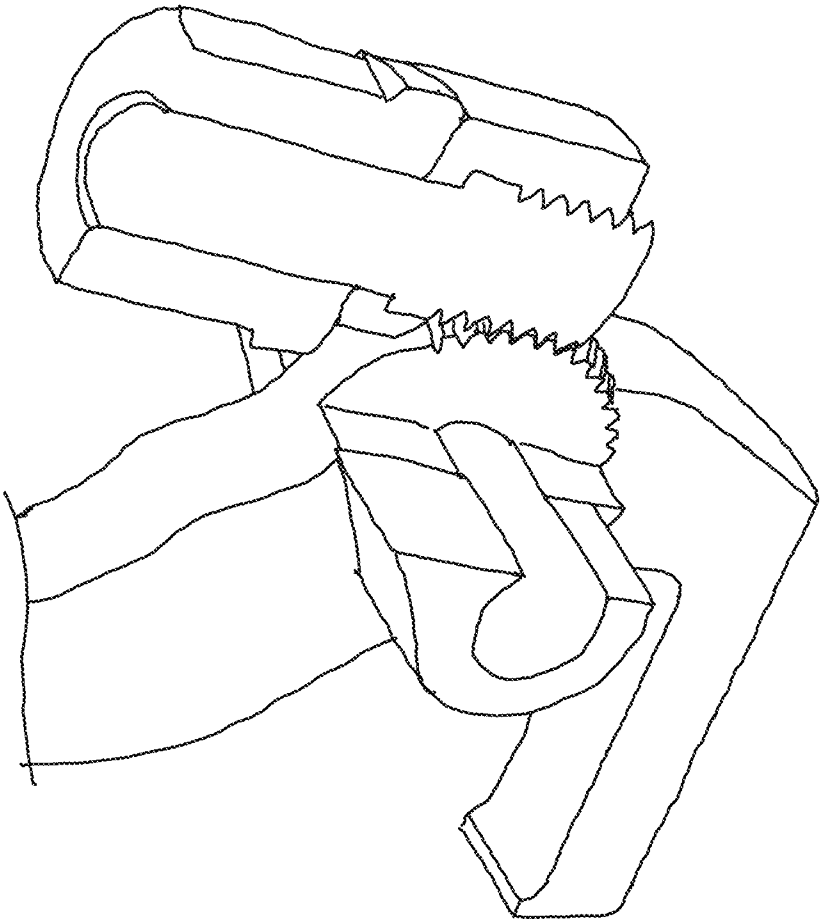
FIG. 32 is a section view of an actuation mechanism of the pedicle screw distractor and reduction instrument of FIG. 31, according to some implementations.
Figure 33:
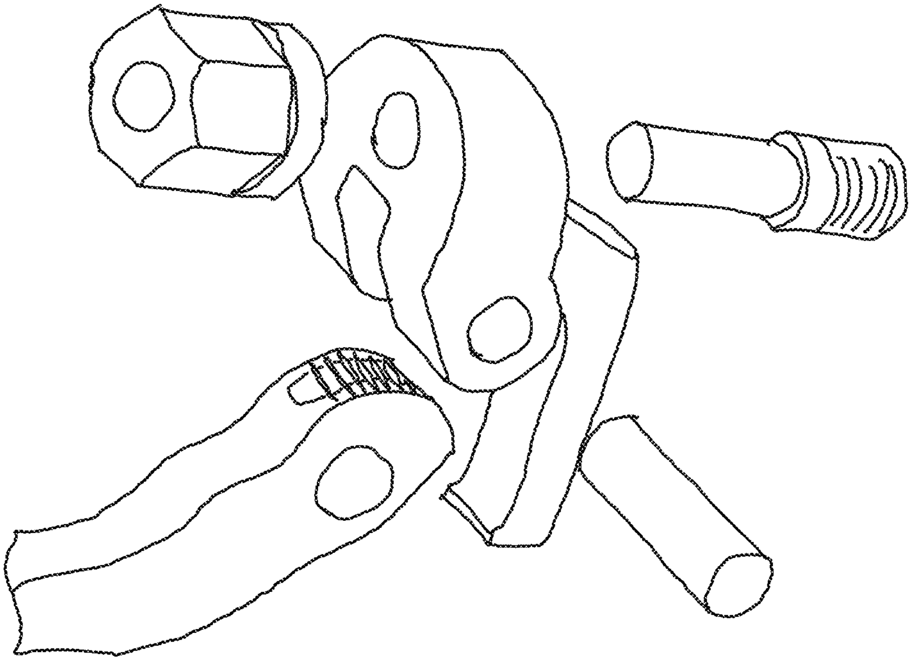
FIG. 33 is an exploded view of an actuation mechanism of the pedicle screw distractor and reduction instrument of FIG. 31, according to some implementations.

As shown in FIGS. 31-33, the distraction actuator and/or the reduction actuator can include a worm gear arrangement that provides positive engagement and position holding while still providing the user the ability to slowly move the proximal anchor 118 and the distal anchor 134 as desired.

Figure 34:
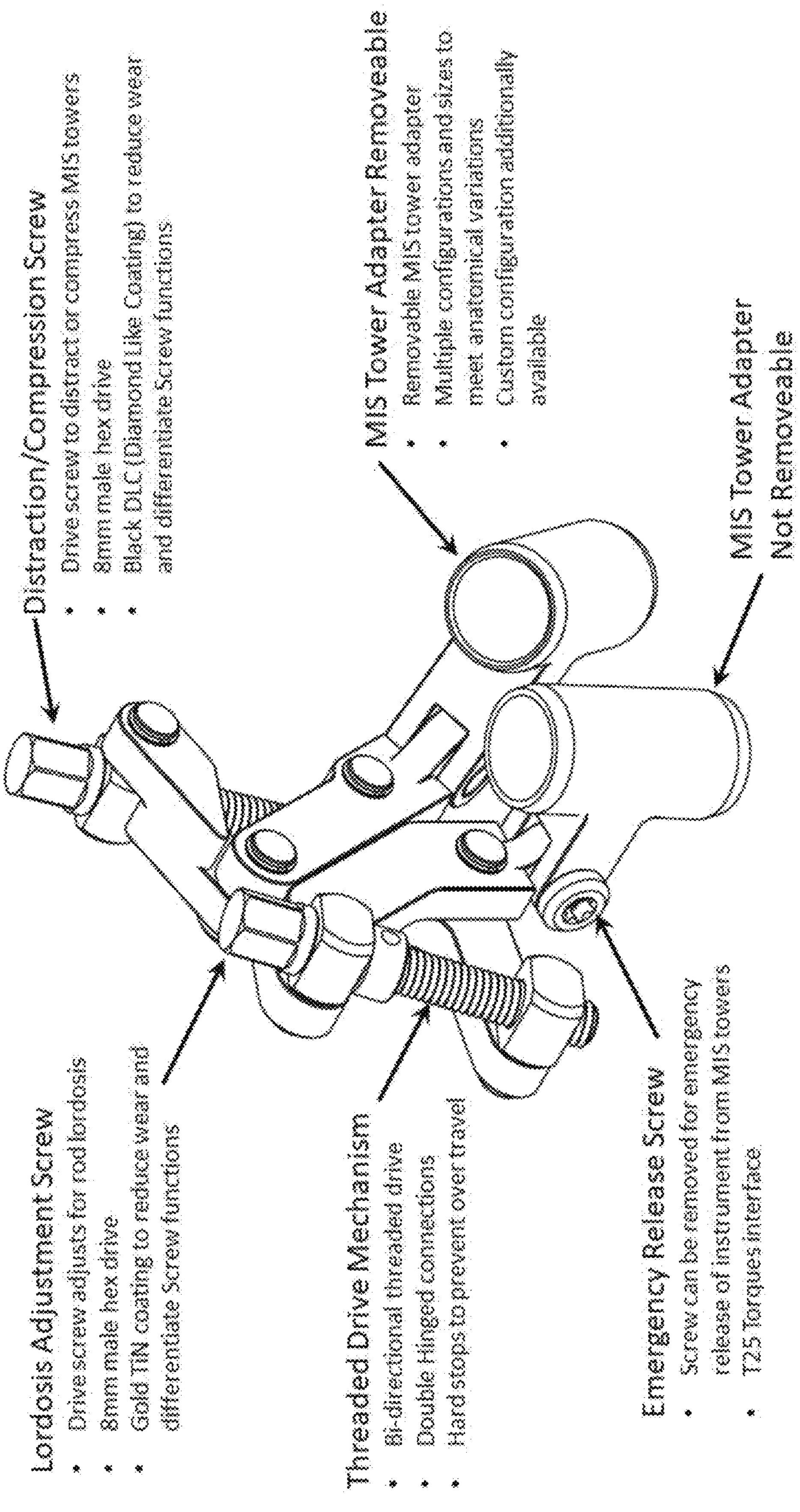
FIG. 34 is a perspective view of another pedicle screw distractor and reduction instrument, according to some implementations.
Figures 35, 36:
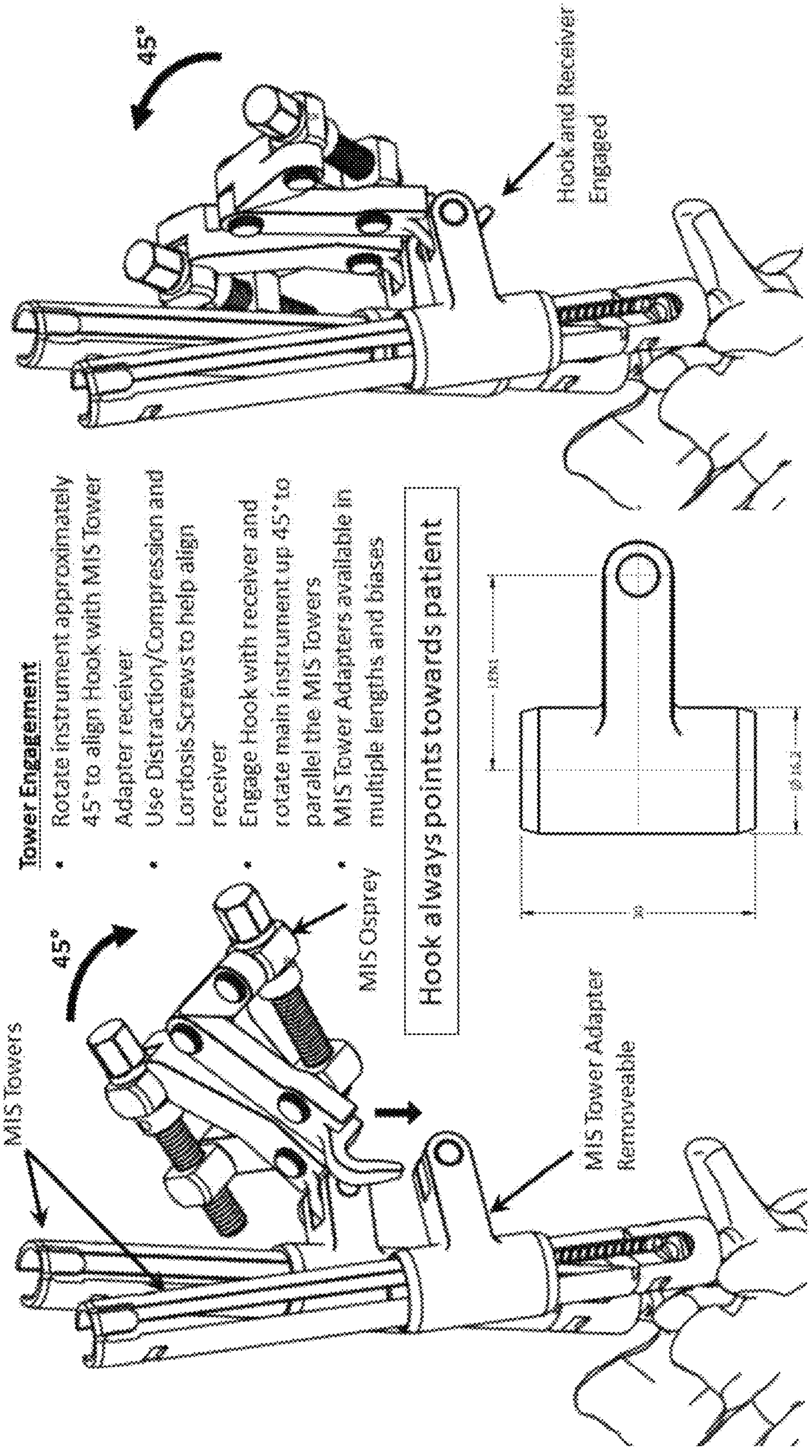
Figure 39:
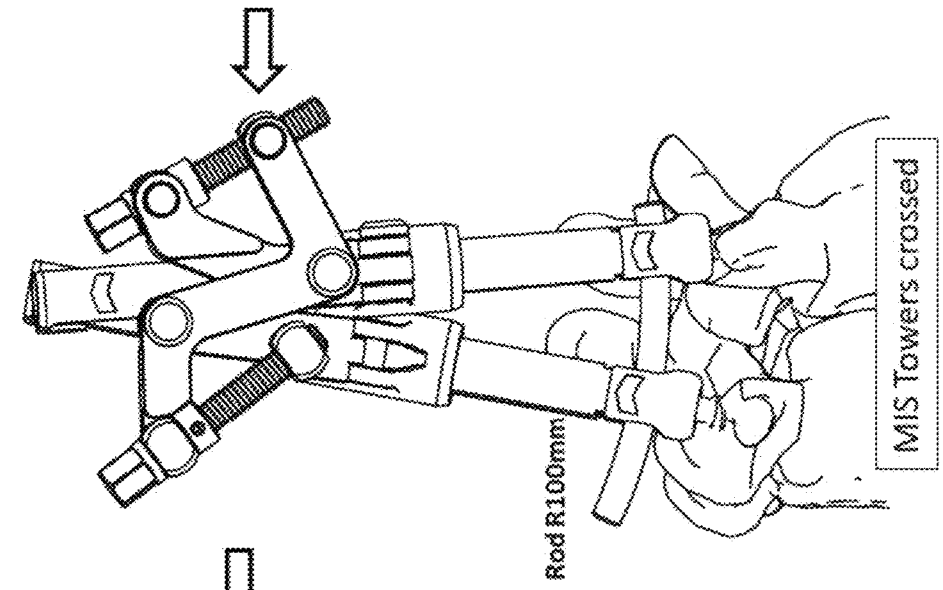
Figure 38:
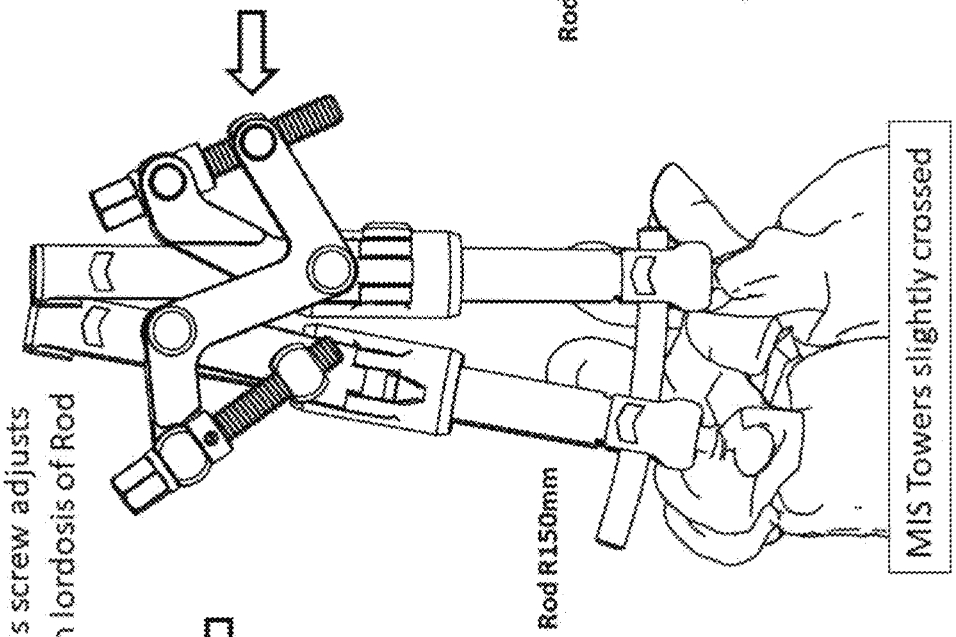
Figure 37:
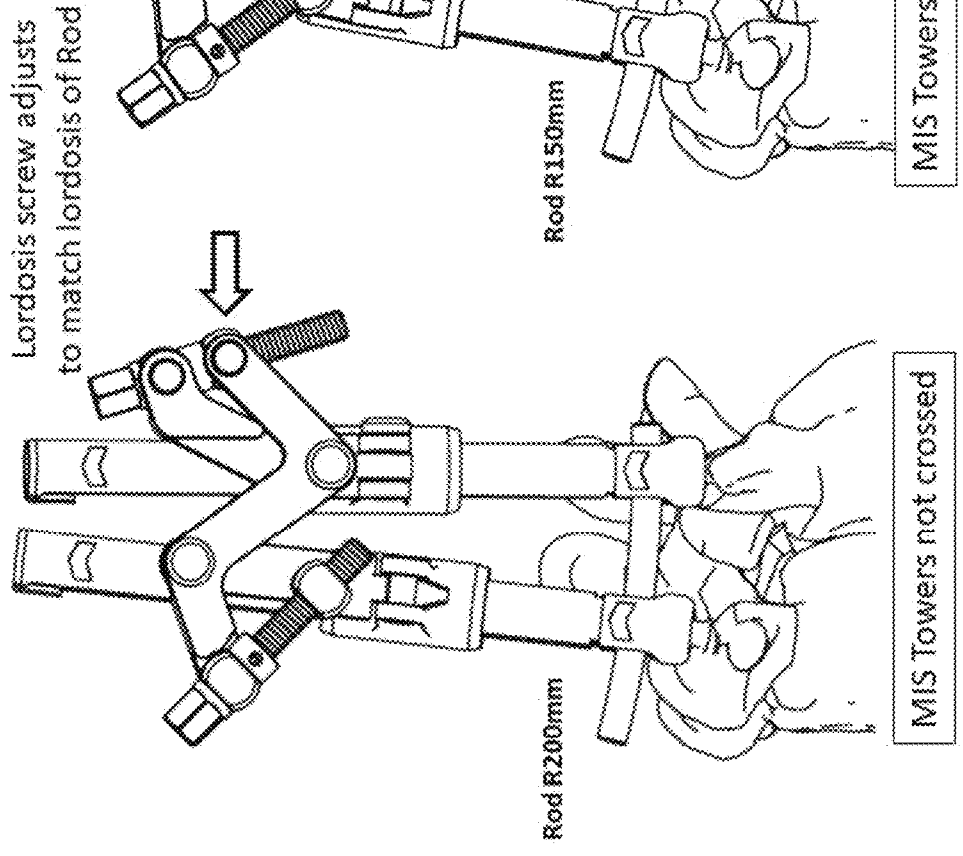
Figure 40:
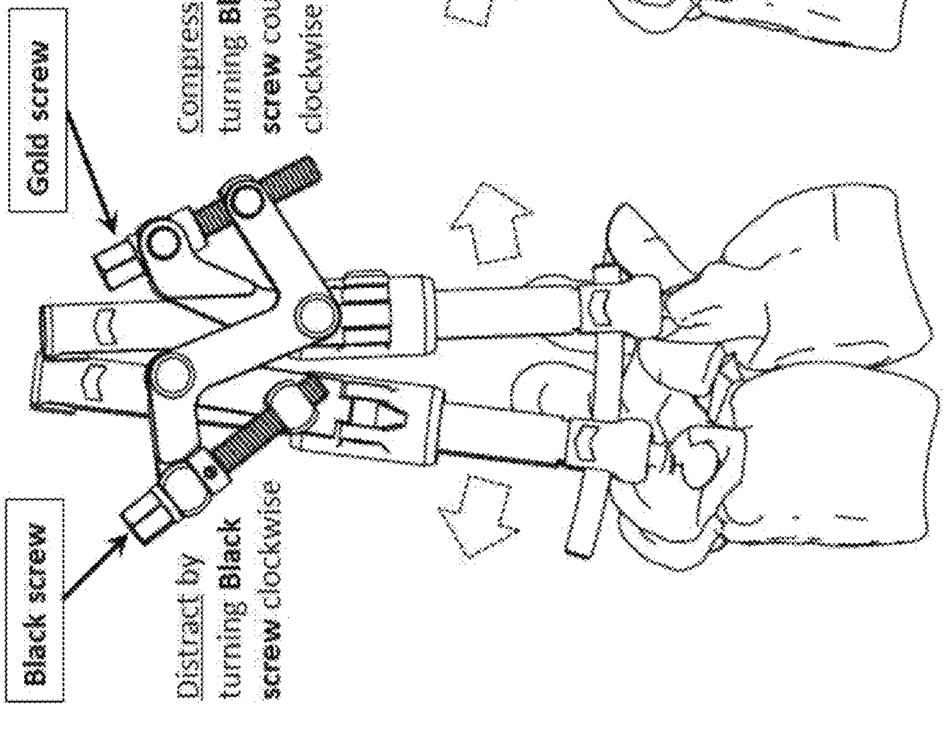
Figure 41:
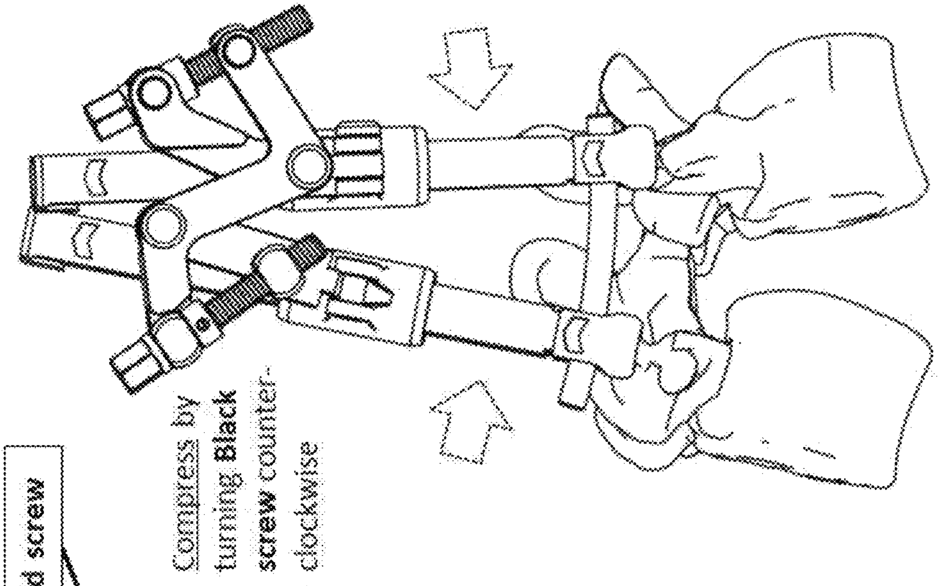
Figure 42:
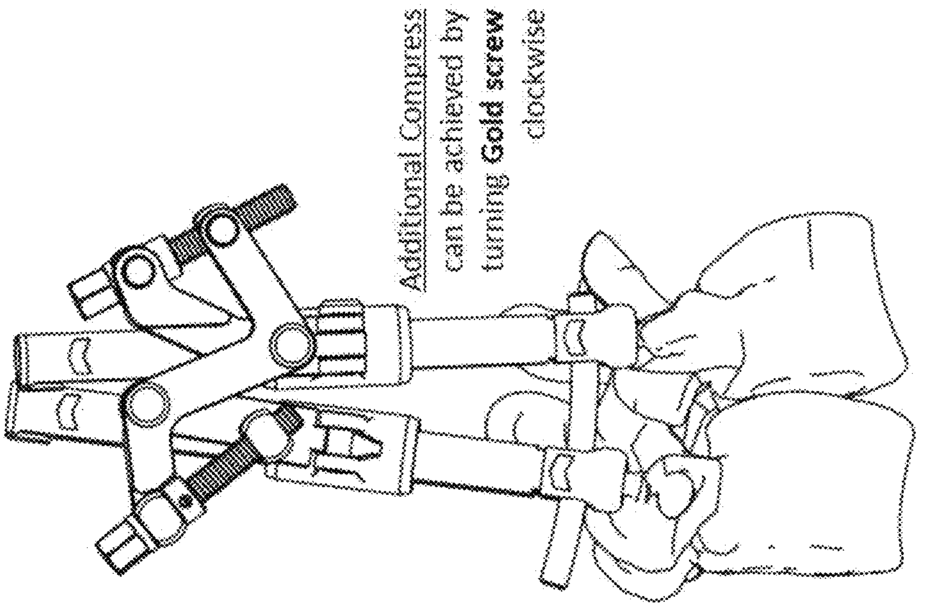

FIGS. 34-35 show another pedicle screw distractor and reduction instrument for use in minimally invasive surgery.

For purposes of this description, certain advantages and novel features of the aspects and configurations of this disclosure are described herein. The described methods, systems, and apparatus should not be construed as limiting in any way. Instead, the present disclosure is directed toward all novel and nonobvious features and aspects of the various disclosed aspects, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present or problems be solved.

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on the software and hardware systems chosen and on designer choice. All such variations are within the scope of the disclosure. Likewise, software implementations of the described methods could be accomplished with standard programming techniques with rule-based logic and other logic to accomplish the various connection steps, processing steps, comparison steps, and decision steps.

Features disclosed in this specification (including any accompanying claims, abstract, and drawings), and/or all of the steps of any method or process so disclosed, may be combined in any combination, except combinations where at least some of such features and/or steps are mutually exclusive. The claimed features extend to any novel one, or any novel combination, of the features disclosed in this specification (including any accompanying claims, abstract, and drawings), or to any novel one, or any novel combination, of the steps of any method or process so disclosed.

As used in the specification and the appended claims, the singular forms “a”, “an”, and “the” include plural referents unless the context clearly dictates otherwise. Ranges may be expressed herein as from “about” one particular value, and/or to “about” another particular value. When such a range is expressed, another aspect includes from the one particular value and/or to the other particular value. Similarly, when values are expressed as approximations, by use of the antecedent “about”, it will be understood that the particular value forms another aspect. It will be further understood that the endpoints of each of the ranges are significant both in relation to the other endpoint, and independently of the other endpoint. The terms “about” and “approximately” are defined as being “close to” as understood by one of ordinary skill in the art. In one non-limiting aspect the terms are defined to be within 10%. In another non-limiting aspect, the terms are defined to be within 5%. In still another non-limiting aspect, the terms are defined to be within 1%.

The terms “coupled”, “connected”, and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another. If “coupled” or variations thereof are modified by an additional term (e.g., directly coupled), the generic definition of “coupled” provided above is modified by the plain language meaning of the additional term (e.g., “directly coupled” means the joining of two members without any separate intervening member), resulting in a narrower definition than the generic definition of “coupled” provided above. Such coupling may be mechanical, electrical, or fluidic. For example, circuit A communicably “coupled” to circuit B may signify that the circuit A communicates directly with circuit B (i.e., no intermediary) or communicates indirectly with circuit B (e.g., through one or more intermediaries).

Certain terminology is used in the following description for convenience only and is not limiting. The words “right”, “left”, “lower”, and “upper” designate direction in the drawings to which reference is made. The words “inner” and “outer” refer to directions toward and away from, respectively, the geometric center of the described feature or device. The words “distal” and “proximal” refer to directions taken in context of the item described and, with regard to the instruments herein described, are typically based on the perspective of the practitioner using such instrument, with “proximal” indicating a position closer to the practitioner and “distal” indicating a position further from the practitioner. The terminology includes the above-listed words, derivatives thereof, and words of similar import.

Throughout the description and claims of this specification, the word “comprise” and variations of the word, such as “comprising” and “comprises”, means “including but not limited to”, and is not intended to exclude, for example, other additives, components, integers or steps. “Exemplary” means “an example of” and is not intended to convey an indication of a preferred or ideal aspect. “Such as” is not used in a restrictive sense, but for explanatory purposes.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention.

EXEMPLARY IMPLEMENTATIONS

Example 1: A pedicle screw distractor/reduction instrument including: a distal anchor, main body, reduction screw, secondary linkage, drive linkage, poly nut, proximal bar, and proximal anchor.

Example 2: The instrument of any of the previous examples, wherein the distal anchor anchors to distal pedicle screw.

Example 3: The instrument of any of the previous examples, wherein the distal anchor is received within the saddle portion of the pedicle screw tulip and locking caps is used to secure the distal anchor within the saddle and within the distal pedicle screw tulip.

Example 4: The instrument of any of the previous examples, wherein the distal anchor is sized and configured to couple to a mono-axial and/or poly-axial pedicle screw.

Example 5: The instrument of any of the previous examples, wherein U-shaped cross-section of the foot of the distal anchor is used to provide stability by not allowing axial rotation of the foot of the distal anchor within the rod slot of the distal pedicle screw while both attaching and operating the distractor/reduction instrument Example 6: The instrument of any of the previous examples, wherein a hinged joint between the main bar/body to be lifted (rotated) creating a reduction force on the distal pedicle screw and corresponding distal vertebral body.

Example 7: The instrument of any of the previous examples, wherein the reduction screw (jack screw) drives the main body to cause lift (reduction) of the distal anchor/distal pedicle screw/distal vertebral body.

Example 8: The instrument of any of the previous examples, wherein the distal anchor and the main body are pivotably coupled, wherein the distal anchor includes an arm opposite the anchor foot extending beyond the coupling point of the distal anchor and the main body, the arm including an opening (e.g., female threaded opening) that engages a reduction screw (jack screw), where the main body includes a foot extending beyond the coupling point of the distal anchor and the main body, wherein engagement between the reduction screw and the opening in the distal anchor arm causes the distal end of the reduction screw to engage the foot of the main body (downward directed force), thereby resulting in a corresponding upward directed force on the distal anchor and causing the causing the lifting and reducing the distal pedicle screw/vertebral body.

Example 9: The instrument of any of the previous examples, wherein the threaded end of the reduction screw engages a threaded opening provided on an arm of the distal anchor to apply a force on the main body.

Example 10: The instrument of any of the previous examples, wherein the reduction screw includes a convex end/convex threaded end, where the convex end of the reduction screw engages a corresponding receiving slot/depression on the foot of the main body.

Example 11: The instrument of any of the previous examples, wherein the main body provides the main structure of the distractor/reduction instrument.

Example 12: The instrument of any of the previous examples, wherein the main body includes a U-shaped protrusion that provides a double shear hinged joint to ensure robust and stable rotation of the instrument.

Example 13: The instrument of any of the previous examples, wherein the main body includes a U-shaped protrusion that provides a solid area for a radial channel to receive the convex end of the reduction screw, where as the main body rotates the channel allows the reduction screw to translate smoothly through entire range of motion.

Example 14: The instrument of any of the previous examples, wherein the main body includes a cut out to allow an instrument to engage the pedicle screws locking cap.

Example 15: The instrument of any of the previous examples, wherein the main body includes a second hinge location is used to attach the secondary linkage.

Example 16: The instrument of any of the previous examples, wherein the proximal end of the main body has a receiving feature for the drive linkage.

Example 17: The instrument of any of the previous examples, wherein a recess (e.g., (spherical recess) on the proximal end of the main body is designed to the allow the drive linkage to change orientation when operated.

Example 18: The instrument of any of the previous examples, wherein the recess (e.g., (spherical recess) allows the poly nut to engage the recess on the main body and thread onto the drive linkage.

Example 19: The instrument of any of the previous examples, wherein drive linkage connects the main body to the proximal end of the secondary linkage, which causes distraction when the poly nut is rotated (e.g., rotated clockwise).

Example 20: The instrument of any of the previous examples, wherein the poly nut interfaces the drive linkage to the main body.

Example 21: The instrument of any of the previous examples, wherein the poly nut allows the secondary linkage to change angles while the poly nut is rotated.

Example 22: The instrument of any of the previous examples, wherein the stop nut is provided at the end of the drive linkage to prevent the poly nut from disengaging.

Example 23: The instrument of any of the previous examples, wherein the drive linkage is coupled to the proximal end of the secondary linkage.

Example 24: The instrument of any of the previous examples, wherein the proximal bar is located between (e.g., sandwiched between) the drive linkage and the secondary linkage.

Example 25: The instrument of the previous examples, wherein the components are connected via a shaft that allows axial rotation of the joint.

Example 26: The instrument of any of the previous examples, wherein the proximal bar connects the proximal anchor to the main body.

Example 27: The instrument of any of the previous examples, wherein the proximal bar includes a recess (e.g., spherical recess) at the proximal end where the proximal anchor is captured.

Example 28: The instrument of any of the previous examples, wherein the proximal anchor is retained by a poly nut, where the poly nut interfaces with the recess (e.g., spherical recess) of the Proximal Bar.

Example 29: The instrument of any of the previous examples, wherein the poly nut can poly angulate up to 30° (e.g., 15°) in all direction when poly nut is not fully tightened.

Example 30: The instrument of any of the previous examples, wherein, when poly nut is mostly tightened, the proximal anchor is drawn towards the recess (e.g., spherical recess), forcing the proximal anchor more normal to the proximal bar, and the proximal anchor can still rotate around the threaded axis of the anchor Example 31: The instrument of any of the previous examples, wherein, when the Poly Nut is fully tightened, the Proximal Anchor resists both axial and poly-axial motion.

Example 32: The instrument of any of the previous examples, wherein proximal bar at the distal connection to the instrument is a welded shaft.

Example 33: The instrument of any of the previous examples, wherein the axis of the Secondary Linkage, Proximal Bar and Drive Linkage are aligned and secured with a welded shaft Example 34: The instrument of any of the previous examples, wherein the primary rotation axis of the Proximal Bar is always allowed to rotate freely.

Example 35: The instrument of any of the previous examples, wherein the Proximal Anchor connects proximal pedicle screw to main Distraction/Reduction instrument.

Example 36: The instrument of any of the previous examples, wherein the Proximal Anchors functions like Distal Anchor's connection.

Example 37: The instrument of any of the previous examples, wherein the threaded arm of the Proximal Anchor is always orientated towards the cranial side.

Example 38: The instrument of any of the previous examples, wherein the Anchor is designed to be used with a counter torque to allows orientation of the tulip and the Proximal Anchor.

Example 39: The instrument of any of the previous examples, wherein the distal pedicle screw is torqued after the proximal anchor is connected to the instrument, as a result the entire instrument acts as its own counter torque.

Example 40: The instrument of any of the previous examples, wherein the main bar has an relieved area to allow a driver shaft to access the locking cap of the distal and/or proximal pedicle screw.

Example 41: The instrument of any of the previous examples, wherein the locking cap on both the proximal and distal pedicle screws are torqued to manufacturers specifications.

Example 42: The instrument of any of the previous examples, including multiple proximal anchors designs available to adapt to various patient physiologies.

Example 43: The instrument of any of the previous examples, wherein the length and angle of the threaded arm can be varied to meet complex anatomies.

Example 44: The instrument of any of the previous examples, wherein the proximal anchors can be angled left or right for complex reductions.

Example 45: The instrument of any of the previous examples, wherein the cross section of the proximal anchors foot is the standard U-shaped.

Example 46: The instrument of any of the previous examples, wherein the cross-section of the proximal anchor foot includes a cylinder shaped and/or polygon shaped.

Example 47: The instrument of any of the previous examples, wherein the proximal anchor includes a threaded arm that is connected to the proximal bar with poly nut.

Example 48: The instrument of any of the previous examples, wherein any of the instrument components are extended to provide for a longer instrument and distract over multiple levels of the spine.

Example 49: The instrument of any of the previous examples, wherein any one of the instrument components is sized and configured for use with extended tab pedicle screws.

Example 50: The instrument of any of the previous examples, wherein any one of the instrument components is sized and configured for use with minimally invasive surgery (MIS) pedicle screws.

What is claimed is:

1. A pedicle screw distractor and reduction instrument comprising:

- a main body defining a first pivot axis and a second pivot axis, the main body including:
  - a central bar extending between the first pivot axis and the second pivot axis,
  - a distraction tab extending from the central bar and defining a distraction aperture, and
  - a reduction foot extending from the central bar and defining a race;
- a secondary link pivotably mounted to the main body at the first pivot axis and defining a third pivot axis spaced apart from the first pivot axis and the second pivot axis;
- a drive link coupled to the secondary link at the third pivot axis and received within the distraction aperture;
- a distraction actuator coupled to the drive link and structured to move the main body relative the secondary link about the first pivot axis;
- a proximal bar pivotably coupled to the secondary link about the third pivot axis and defining a proximal bar aperture;
- a proximal anchor received through the proximal bar aperture and including a proximal anchor foot configured to engage a proximal pedicle screw;
- a distal anchor pivotably coupled to the main body about the second pivot axis and including:
  - a distal anchor tab, and
  - a distal anchor foot configured to engage a distal pedicle screw; and
- a reduction actuator engaged with the distal anchor tab and the race of the reduction foot to move the distal anchor foot relative to the main body about the second pivot axis.

2. The pedicle screw distractor and reduction instrument of claim 1, wherein the distal anchor foot defines a U-shaped cross section.

3. The pedicle screw distractor and reduction instrument of claim 1, wherein the reduction actuator includes a cam follower head shaped to engage the race.

4. The pedicle screw distractor and reduction instrument of claim 1, wherein the distraction aperture includes a centering feature.

5. The pedicle screw distractor and reduction instrument of claim 1, wherein the proximal bar aperture includes a centering feature.

6. The pedicle screw distractor and reduction instrument of claim 1, wherein the proximal anchor includes a proximal anchor thread extending through the proximal bar aperture, and the pedicle screw distractor and reduction instrument further comprising a poly-nut engaged with the proximal anchor thread.

7. The pedicle screw distractor and reduction instrument of claim 1, wherein the proximal anchor can rotate relative to the proximal bar by up to 15 degrees.

8. The pedicle screw distractor and reduction instrument of claim 1, wherein the proximal bar rotates freely about the third pivot axis relative to the secondary link and the drive link.

9. The pedicle screw distractor and reduction instrument of claim 1, wherein the drive link includes distraction threads and the distraction actuator includes a distraction nut engaged with the distraction threads.

10. The pedicle screw distractor and reduction instrument of claim 1, wherein the distal anchor tab includes a distal anchor threaded aperture and the reduction actuator includes a reduction screw threadingly engaged with the distal anchor threaded aperture.

11. The pedicle screw distractor and reduction instrument of claim 1, wherein the drive link includes a hard stop at a maximum expansion position and a hard stop at a minimum expansion position.

12. The pedicle screw distractor and reduction instrument of claim 1, further comprising:

a first pin coupling the main body and the secondary link along the first pivot axis;

a second pin coupling the main body and the distal anchor along the second pivot axis; and a third pin coupling the secondary link and the proximal bar along the third pivot axis.

13. The pedicle screw distractor and reduction instrument of claim 12, further comprising a biasing element coupled between the distraction tab and the third pin to bias the distraction tab away from the third pivot axis.

14. The pedicle screw distractor and reduction instrument of claim 1, wherein the proximal anchor includes a left offset or a right offset.

15. The pedicle screw distractor and reduction instrument of claim 1, wherein the distal anchor rotates relative to the main body up to 50 degrees about the second pivot axis.

16. A pedicle screw distractor and reduction instrument comprising:

a main body including a distraction tab and a reduction foot;

a secondary link pivotably mounted to the main body;

a drive link coupled between the secondary link and the distraction tab;

a distraction actuator coupled to the drive link and structured to move the main body relative the secondary link;

a proximal anchor pivotably coupled to the secondary link and including a proximal anchor foot configured to engage a proximal pedicle screw;

a distal anchor pivotably coupled to the main body and including a distal anchor foot configured to engage a distal pedicle screw; and a reduction actuator engaged between the reduction foot and the distal anchor to move the distal anchor foot relative to the main body.

17. The pedicle screw distractor and reduction instrument of claim 16, wherein the drive link includes a hard stop at a maximum expansion position and a hard stop at a minimum expansion position.

18. The pedicle screw distractor and reduction instrument of claim 16, wherein the distal anchor rotates relative to the main body up to 50 degrees.

19. The pedicle screw distractor and reduction instrument of claim 16, further comprising a proximal bar supporting the proximal anchor and coupled to the secondary link to rotates freely relative to the secondary link and the drive link.

20. A method comprising:

seating a proximal anchor within a saddle of a proximal pedicle screw;

coupling a proximal locking cap to the proximal pedicle screw;

seating a distal anchor within a saddle of a distal pedicle screw;

coupling a distal locking cap to the distal pedicle screw;

inserting a proximal anchor thread of the proximal anchor into a proximal bar aperture provided in a proximal bar;

coupling a proximal nut to the proximal anchor thread;

rotating a distraction nut to expand a distractor by pulling the distal anchor and the proximal anchor apart; and rotating a reduction screw to move the distal anchor relative to a main body.

* * * * *